(12) United States Patent
Huang et al.

(10) Patent No.: US 10,197,523 B2
(45) Date of Patent: Feb. 5, 2019

(54) METHOD FOR ESTIMATING DISTRIBUTION OF SAMPLE

(71) Applicant: Bionime Corporation, Dali (TW)

(72) Inventors: Chun-Mu Huang, Sanchung (TW); Cheng-Teng Hsu, Dali (TW)

(73) Assignee: Bionime Corporation, Dali (TW)

( * ) Notice: Subject to any disclaimer, the term of this patent is extended or adjusted under 35 U.S.C. 154(b) by 72 days.

(21) Appl. No.: 15/299,605

(22) Filed: Oct. 21, 2016

(65) Prior Publication Data

US 2017/0038330 A1 Feb. 9, 2017

Related U.S. Application Data

(63) Continuation of application No. 12/757,695, filed on Apr. 9, 2010, now abandoned.

(30) Foreign Application Priority Data

Apr. 9, 2009 (TW) .............................. 098111902 A

(51) Int. Cl.
*G01N 27/327* (2006.01)
*G01N 27/404* (2006.01)

(52) U.S. Cl.
CPC ..... *G01N 27/3272* (2013.01); *G01N 27/3273* (2013.01); *G01N 27/404* (2013.01); *G01N 27/3271* (2013.01)

(58) Field of Classification Search
CPC .......... C12Q 1/00; C12Q 1/001; C12Q 1/004; C12Q 1/005; C12Q 1/006; C12Q 1/26; C12Q 1/34; C12Q 1/54; G01N 27/48; G01N 27/26; G01N 27/327–27/3274; G01N 33/487; G01N 33/49; A61B 5/14532; A61B 5/14535; A61B 5/14536
See application file for complete search history.

(56) References Cited

U.S. PATENT DOCUMENTS

| | | | |
|---|---|---|---|
| 5,266,179 | A | 11/1993 | Nankai et al. |
| 5,352,351 | A | 10/1994 | White et al. |
| 5,366,609 | A | 11/1994 | White et al. |
| 6,878,251 | B2 | 4/2005 | Hodges et al. |
| 2006/0175199 | A1 | 8/2006 | Huang |
| 2007/0017824 | A1 | 1/2007 | Rippeth et al. |
| 2007/0272564 | A1 | 11/2007 | Huang |
| 2008/0179197 | A1 | 7/2008 | Wu |

FOREIGN PATENT DOCUMENTS

| | | |
|---|---|---|
| EP | 1236995 | 9/2002 |
| EP | 1443322 | 8/2004 |
| EP | 1272833 | 11/2004 |
| EP | 1605253 | 12/2005 |
| EP | 1860432 | 11/2007 |
| WO | 2006109277 | 10/2006 |
| WO | 2008040982 | 4/2008 |
| WO | 2008040998 | 4/2008 |

*Primary Examiner* — Maris R Kessel
(74) *Attorney, Agent, or Firm* — Volpe and Koenig, P.C.

(57) ABSTRACT

The present invention relates to a method for estimating a distribution of a sample flowed from a first electrode toward a second electrode of an electrochemical test strip. A working voltage is provided between the first electrode and the second electrode for obtaining a first and a second currents, where a ratio of the first current to the second current is applied to estimate the distribution of the sample on the first and the second electrodes and an effectiveness of a measurement of a target analyte of the sample.

19 Claims, 28 Drawing Sheets

METHOD FOR ESTIMATING DISTRIBUTION OF SAMPLE

CROSS REFERENCE TO RELATED APPLICATIONS

This application is a continuation of U.S. application Ser. No. 12/757,695, which was filed Apr. 9, 2010 and claimed the benefit of Taiwanese Application No. 098111902 filed Apr. 9, 2009, both of which are incorporated herein by reference as if fully set forth.

TECHNICAL FIELD

The present invention is related to a method for estimating the effectiveness of the test and/or the measurement performed by a meter. In particular, the present method uses a ratio obtained from a series of values of currents to reveal the distribution of a target sample covered on the electrodes of an electrochemical test apparatus, e.g. an electrochemical test strip, and estimate the effectiveness of the test and/or the measurement performed by the meter being inserted with the electrochemical test strip.

DESCRIPTION OF RELATED ART

Electrochemical sensing systems for analyzing analytes in a biological samples are widely used. For example, analytes such as glucose level, cholesterol level or uric in a sample such as blood may be analyzed. Generally speaking, such electrochemical sensor systems include a test strip and a measuring meter. In particular, those test strips are provided as single use and disposable ones for easy home use.

The electrochemical sensor using enzymatic amperometric methods are well known. The sensors of such systems have electrodes which are coated with a reagent including enzymes. The electrodes are used to sense an electrochemical current which is produced by a reaction between the reagent and the analyte(s) in a test sample.

The enzyme is used for a unity, well specified reaction with a specific analyte in the test sample. This specific reaction reduces the interference with other analytes. For example, a reagent with a specific cholesterol enzyme may be used to test cholesterol level in a sample. A reagent with a glucose oxidase may be used to measure the glucose level in a blood sample.

The glucose oxidase does not react with the cholesterol, nor with other sugars in the blood sample. The use of glucose oxidase e.g. typically leads to a 99% unique selection of glucose within the sample. Methods based on the use of enzyme are leading to most accurate measurement results.

In the method for determining the concentration of the analyte in the sample by the sensing current, the sensing current is measured and called the Cottrell current. The Cottrell current is obtained by the following equation (Cottrell Equation).

$$i(t) = K \cdot n \cdot F \cdot A \cdot C \cdot D^{0.5} \cdot t^{-0.5}$$

Where, i is an instant value of the sensing current;
K is a constant;
n is the transferred number of electrons;
F is the Faraday constant;
A is the surface area of the working electrode;
C is the concentration of the analyte in the sample;
D is the diffusion coefficient of the reagent; and
t is a specific time after a predetermined voltage has been applied to the electrodes.

Generally speaking, as to the constructions of known disposable electrochemical test strips and measurement procedures thereof, the following elements/steps are included.

1. A base sheet is used to be the substrate.
2. At least two separate electrodes are configured in the base sheet, where both the two separate electrodes have two terminals, a first and a second terminals. The first and the second terminals of the first one of the electrodes are used to be a "working electrode" and an output terminal of the working electrode respectively, wherein the output terminal of the working electrode is electrically connected to a measuring meter. The first and the second terminals of the second one of the conductive electrodes are used to be a "counter electrode" and an output terminal of the counter electrode respectively, wherein the output terminal of the counter electrode is electrically connected to the measuring meter. The working electrode and the counter electrode are near configured on the base sheet to form an electrode measuring region.
3. The electrode measuring region is coated with chemical reagents including the enzyme and used to chemically react with a specific analyte in fluid sample.
4. A working voltage provided by the measuring meter is applied between the working electrode and the counter electrode. The working voltage and the polarity thereof are used to make the chemical reaction is under the oxidative state (where the working voltage applied on the working electrode is positive at this time) or reductive state (where the working voltage applied on the working electrode is negative at this time). During the oxidative state or the reductive state, the electrochemical current of the chemical reaction can be measured and such the electrochemical current is the Cottrell current.
5. The concentration of the specific analyte can be obtained by the measured electrochemical current (Cottrell current) and the above-mentioned Cottrell Equation ($i(t) = K \cdot n \cdot F \cdot A \cdot C \cdot D^{0.5} \cdot t^{-0.5}$).

The chemical reagent with the enzyme coated on the working electrode is used to generate a chemical reaction with the specific analyte in the fluid sample. Then, the working voltage is applied on the surface of the working electrode when the chemical reaction reacts and thus the electrochemical current generated on the oxidative region (or the reductive region) can be measured and is the called Cottrell current. The counter electrode is used to be the relative current loop when measuring the electrochemical current (the Cottrell current).

The value of the working voltage applied in the chemical reaction can be chosen from the known cyclic voltammograms to obtain the appropriate oxidative and/or reductive potentials, which is elaborated as follows.

1. Circularly changing the value of the working voltage applied on the working electrode to measure the various values of currents corresponding to the circularly changed the working voltages. From such procedure, the cyclic voltammograms as shown in FIG. 1(A) can be obtained and the Point I reveals the anodic (oxidative) peak current. The voltage corresponding to the anodic peak current (Point I) is the anodic (oxidative) working voltage ($V_I$) which is the most appropriate and sensitive one for the chemical reaction. By applying the anodic working voltage ($V_I$) to the working electrode, the optimum signal to noise ratio (S/N ratio) will be obtained. Point I also reveals the optimum working potential of the oxidative reaction by which the optimum Cottrell current II can be obtained and the S/N ratio will be higher than or equal to 1. If $V_{II}$ (corresponding to Point II)

is applied to the working electrode, the most optimum Cottrell current having the optimum S/N ratio cannot be obtained.

2. The voltage corresponding to the current peak (Point III) of the cyclic voltammograms is the most sensitive cathode (reductive) working voltage ($V_{III}$) for the chemical reaction. Point III reveals the optimum reactive working potential by which the optimum Cottrell current IIII can be obtained and the S/N ratio will be higher than or equal to 1.

3. Selecting the appropriate voltage polarity and the value of the working voltage based on the above-mentioned cyclic voltammograms and procedures to apply thereto the working electrode to measure and obtain the Cottrell current generated by the analytes and the chemical reagents during the oxidation (or the reduction).

It is known from the Cottrell Equation that the concentration of analytes C is proportional to the value of the sensing current i, and therefore that the concentration of analytes C can be obtained by the value i(t) of the sensing current. In addition, because the surface area A of the working electrode is also proportional to the value of the sensing current i, A is taken as a constant for decreasing the variables in the Cottrell Equation. However, the precise definition of the presumption of the surface area A being the constant is "the surface area A is the constant when the electrochemical currents are measured", and therefore the condition, the surface of the working electrode is necessary being totally covered when measuring the electrochemical currents, should be considered for assuring the surface area A of the working electrode is the constant. If the surface of the working electrode is not totally covered by the fluid sample but the surface area A is calculated within the Cottrell Equation, an incorrect value of concentration of analytes C would be obtained.

In brief, the concentration of the analytes in the sample fluid can be obtained and is proportional to the value of the sensing current i. Additionally, since the surface area A of the working electrode is also proportional to the value of the sensing current i, the precisely defined surface area of the working electrode of the test strip is also a key factor for an accurate meter measuring the concentration of analytes in the sample.

Furthermore, the determination as to whether the sample volume distributed in the reaction region of the electrochemical strip is enough is another important factor for the measurement of the concentration of the alanyte in the sample fluid. If there is enough sample fluid distributing in the reaction region of the electrochemical strip, the concentration of the alanyte in the sample fluid can be obtained according to the sensing current i and the Cottrell Equation. On the contrary, if sample fluid is not enough for distributing in the reaction region of the electrochemical strip, the concentration of the alanyte in the sample fluid obtained according to the sensing current i and the Cottrell Equation is an incorrect one. Accordingly, under the circumstance of the surface area of the wording electrode being precisely defined, that whether the sample volume distributed in the reaction region of the electrochemical strip is enough is one of the important factors for the measurement of the concentration of the alanyte in the sample fluid.

Such these sensors (test strips) and meters were disclosed in U.S. Pat. No. 5,266,179, U.S. Pat. No. 5,366,609, or EP 1272833.

The operation principle of the measuring meters disclosed in these patent documents is generally the same. First, a test strip is inserted into the measuring meter. A proper insertion of the test strip within the meter is detected by mechanical and/or electrical switches or contacts. Once a test strip is properly inserted into the measuring meter, the user is asked to provide a sample, typically a drop of blood. The sample of blood is then fed to a reaction zone on the test strip. The reaction zone of the test strip is provided with at least two electrodes which are covered by the reagent.

In order to detect presence of a sample in the reaction zone, a voltage is applied to the electrodes. The resistance of the reagent between the electrodes without the presence of a sample is high. As soon as a sample is present in the reaction region, the resistance between the electrodes (working electrode and counter electrode) is reduced. Reduction of the resistance leads to flow of a current which may be detected as an indication of the presence of a sample.

For a more detailed explanation of the known detecting/measuring methods as above-mentioned, please refer to FIGS. 1(B) and 1(C).

FIG. 1(B) shows the measuring method for the conventional meter, and is also the content of U.S. Pat. No. 5,366,609. FIG. 1(C) is the amplified diagram of scope S shown in FIG. 1(B) and shows the currents generated by the voltage applied to the electrodes on the test strip during the sample detecting period.

As shown in FIG. 1(B), when the test strip is inserted into the meter at time 100, a voltage 102 with a fixed value is applied to the electrodes of the test strip during a sample detecting period 101 for detecting whether a sample is present in the reaction region. Next, a drop of the sample is added to the test strip at time 108.

Please also refer to FIG. 1(C). When the current reaches a sample detecting threshold 112, i.e. the sample is detected being present in the reaction region, a sample volume delaying period 114 starts. In order to estimate whether the sample volume is enough, the meter will continuously applies the voltage 102 to the electrodes of the test strip until time 103.

Then, values of current 109 is compared with a sample volume threshold 113 for determining the end of sample volume delaying period 114. If the value (intensity) of the current is lower than sample volume threshold 113, the meter will alarm to point out that the volume of the sample in the test strip is not enough, and then stops the measurement of the sample.

If there is sufficient sample volume in the reaction region, e.g. revealing by time 115 where value of current 109 is higher than sample volume threshold 113, the meter will start the subsequent step of performing an incubation period 105. During incubation period 105, the meter removes the fixed voltage 102 and does not apply any voltage, i.e. apply a zero voltage 104, to the electrodes of the test strip. In incubation period 105, a specific and predetermined time is provided for the sample to be mixed and dissolved with the reagents coated on the electrodes.

When incubation period 105 finishes, the meter starts a measurement period 106 and apply a predetermined voltage 107 to the electrodes of the test strip during measurement period 106. During measurement period 106, the value of current 110 between the electrodes will be measured.

The determination and the calculation of the concentration of the analyte in the sample is based on the aforementioned Cottrell current, and during measurement period 106 the value of concentration of the analyte in the sample, calculated according to the Cottrell Equation, will be shown on the display of the meter.

Therefore, the definition and determination of sample detecting threshold 112 are very important for estimating whether the sample volume is enough.

Employing experiments and researches full-heartily and persistently, the applicant finally conceived method for estimating distribution of sample.

SUMMARY OF THE INVENTION

The present invention provides a method for estimating the distribution of a sample fluid covering on the surfaces of the electrodes of a electrochemical test apparatus, where the results of the present method can be used for estimating the percentage of the surface of the electrode covered by the sample fluid to estimate the effectiveness and/or correctness of the measurement of the concentration of the analyte in the sample. Moreover, the results of the present method can be used for estimating the above-mentioned effectiveness and/or correctness either prior to the formally measurement of the concentration of the analyte or after the measurement of the concentration of the analyte.

A reaction DC voltage is applied to the electrochemical test apparatus having at least a first and a second electrodes during sample detecting period 101, wherein the reaction DC voltage is determined by the oxidative (or reductive) voltage which is obtained from the cyclic voltammetry and able to make the optimum oxidation (or reduction) of the electrochemical reaction occur.

On another aspect, the present disclosure provides a method for a sensor having at least a first electrode and a second electrode, comprising the steps of (a) providing a target sample flowing from the first electrode to the second electrode; (b) applying a first DC voltage with a voltage value across the first electrode and the second electrode for a first duration to make a potential of the first electrode higher than a potential of the second electrode and to generate a first Cottrell current; (c) removing the first DC voltage; (d) applying a second DC voltage with a voltage value across the first electrode and the second electrode for a second duration to make the potential of the second electrode higher than the potential of the first electrode and to generate a second Cottrell current, wherein the respective voltage values of the first and the second DC voltages are equal; (e) removing the second DC voltage; (f) repeating steps (b) to (e) at least twice; (g) adding up respective values of the first Cottrell currents and respective values of the second Cottrell currents respectively; and (h) obtaining a ratio of a sum of the respective values of the first Cottrell currents over a sum of the respective values of the second Cottrell currents to determine a distribution of the target sample on the first and the second electrodes.

On another aspect, the present disclosure provides a determining method for a distribution of a target sample, comprising the steps of providing a first and a second electrodes; providing the target sample flowing from the first electrode to the second electrode; applying a first DC voltage having a voltage value across the first electrode and the second electrode to make a potential of the first electrode higher than a potential of the second electrode and to generate a first sensing current; removing the first DC voltage; applying a second DC voltage having the voltage value across the first electrode and the second electrode to make the potential of the second electrode higher than the potential of the first electrode and to generate a second sensing current; and obtaining a ratio of a value of the first sensing current over a value of the second sensing current to determine the distribution of the target sample on the first and the second electrodes.

On another aspect, the present disclosure provides a determining method, comprising the steps of providing a first and a second electrodes; providing a target sample flowing from the first electrode to the second electrode; making a potential of the first electrode higher than a potential of the second electrode and to generate a first sensing current; making the potential of the second electrode higher than the potential of the first electrode and to generate a second sensing current; and obtaining a ratio of a value of the first sensing current over a value of the second sensing current to determine the distribution of the target sample on the first and the second electrodes.

DESCRIPTION OF THE EMBODIMENTS

The present invention provides a method for estimating the distribution of a sample fluid covering on the surfaces of the electrodes of a electrochemical test apparatus to estimate the effectiveness and/or correctness of the measurement of the concentration of the analyte in the sample, which can be fully understood and accomplish by the skilled person according to the following embodiments. However, the practice of the present method is not limited into following embodiments.

Figure 1A:
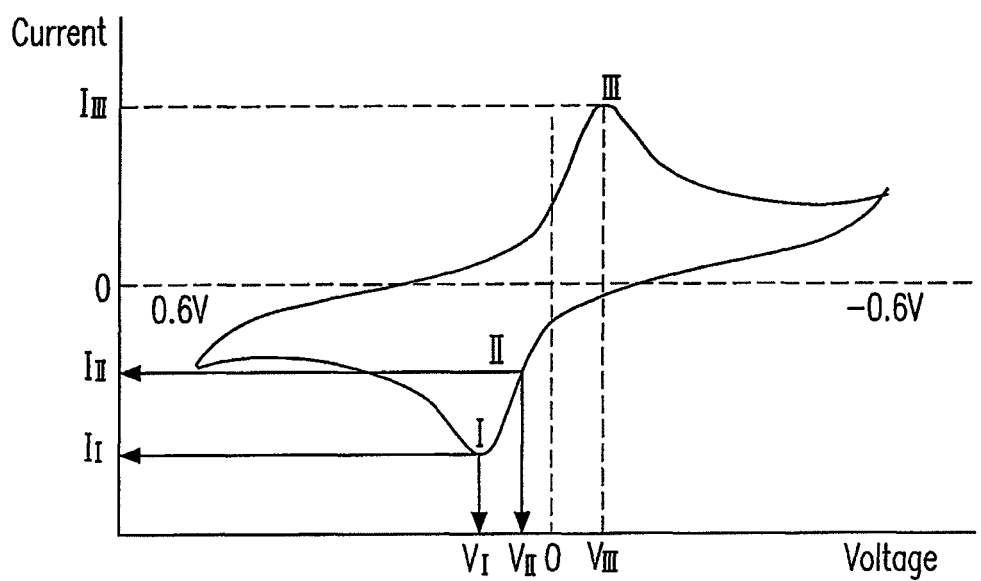
FIG. 1(A) is a known cyclic voltammograms for an electrochemical.
Figure 1B:
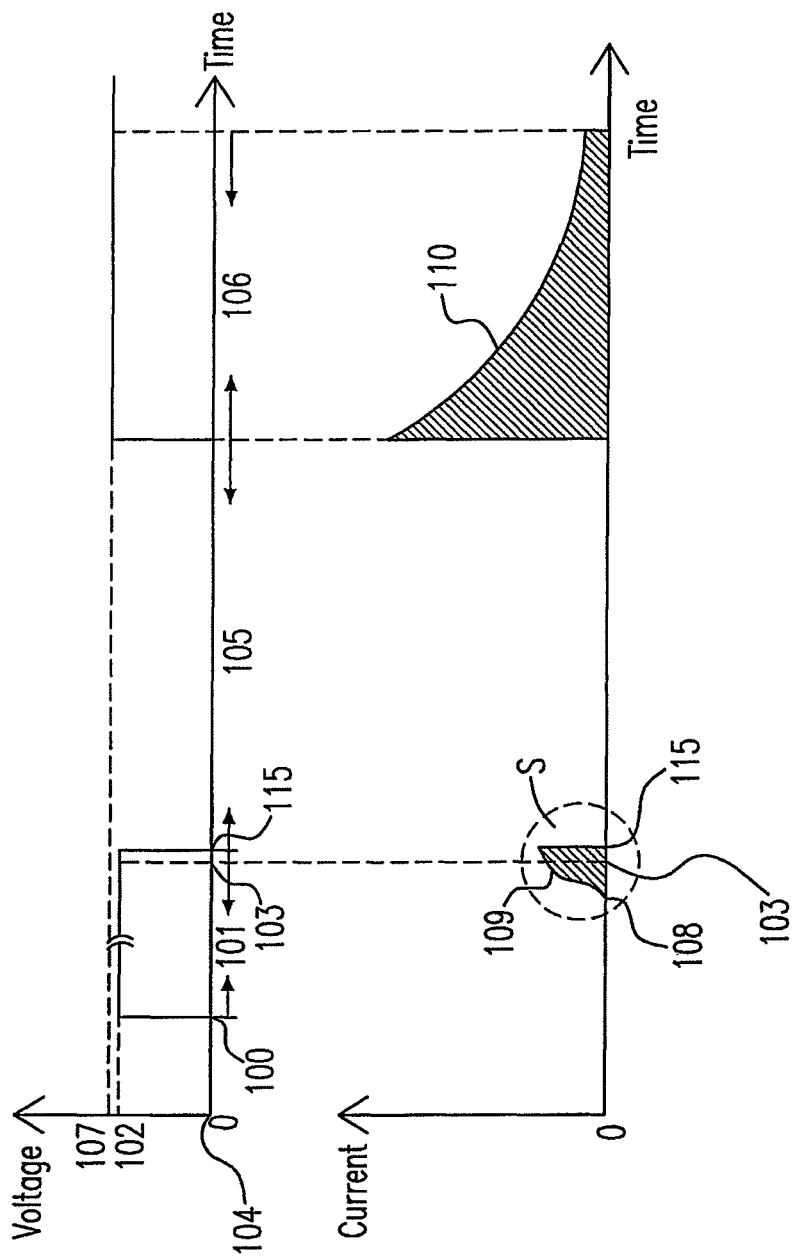
FIG. 1(B) shows the measuring method of U.S. Pat. No. 5,366,609.
Figure 1C:
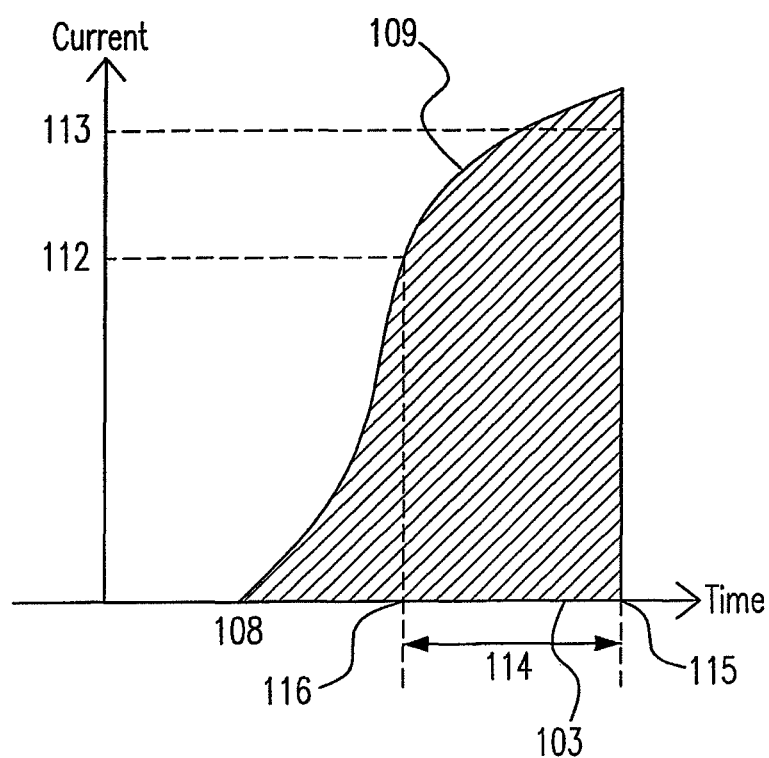
FIG. 1(C) is the amplified diagram of scope S shown in FIG. 1(B).
Figure 2A:
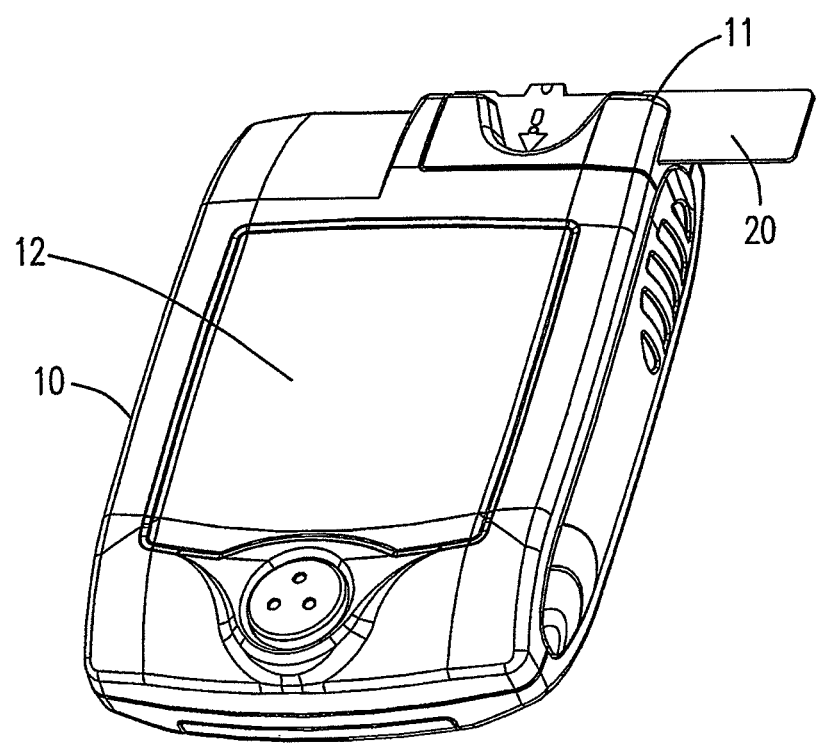
FIG. 2(A) is a schematic diagram of the appearance of meter.
Figure 2B:
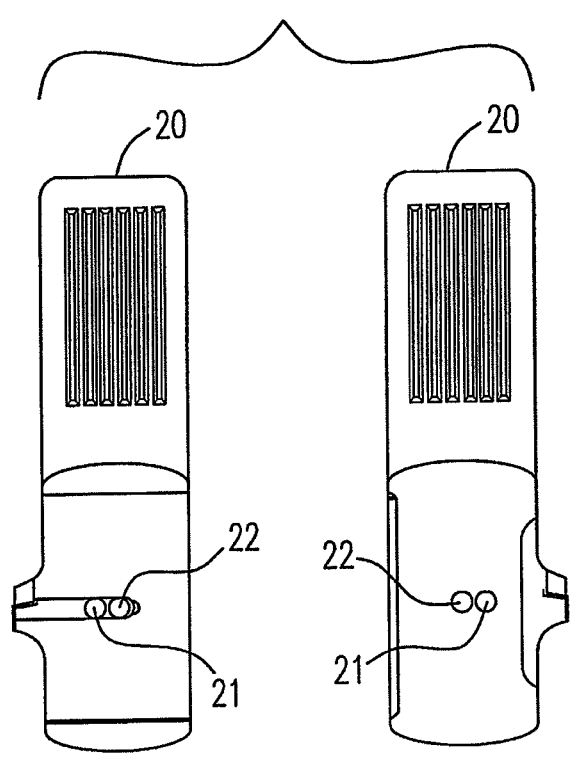
FIG. 2(B) is a schematic diagram showing the front view (the left one) and back view (the right one) of an electrochemical test strip.

Please refer to FIG. 2(A), which shows the appearance of meter 10 applied for the electrochemical test strip. The meter 10 includes a shell with a display 12 showing measurement results, and a slot 11 to be inserted by a sensor, e.g. an electrochemical test strip 20. FIG. 2(B) shows the front view (the left one) and the back view (the right one) of electrochemical test strip 20, wherein electrochemical test strip 20 has electrodes 21 and 22.

Figure 2C:
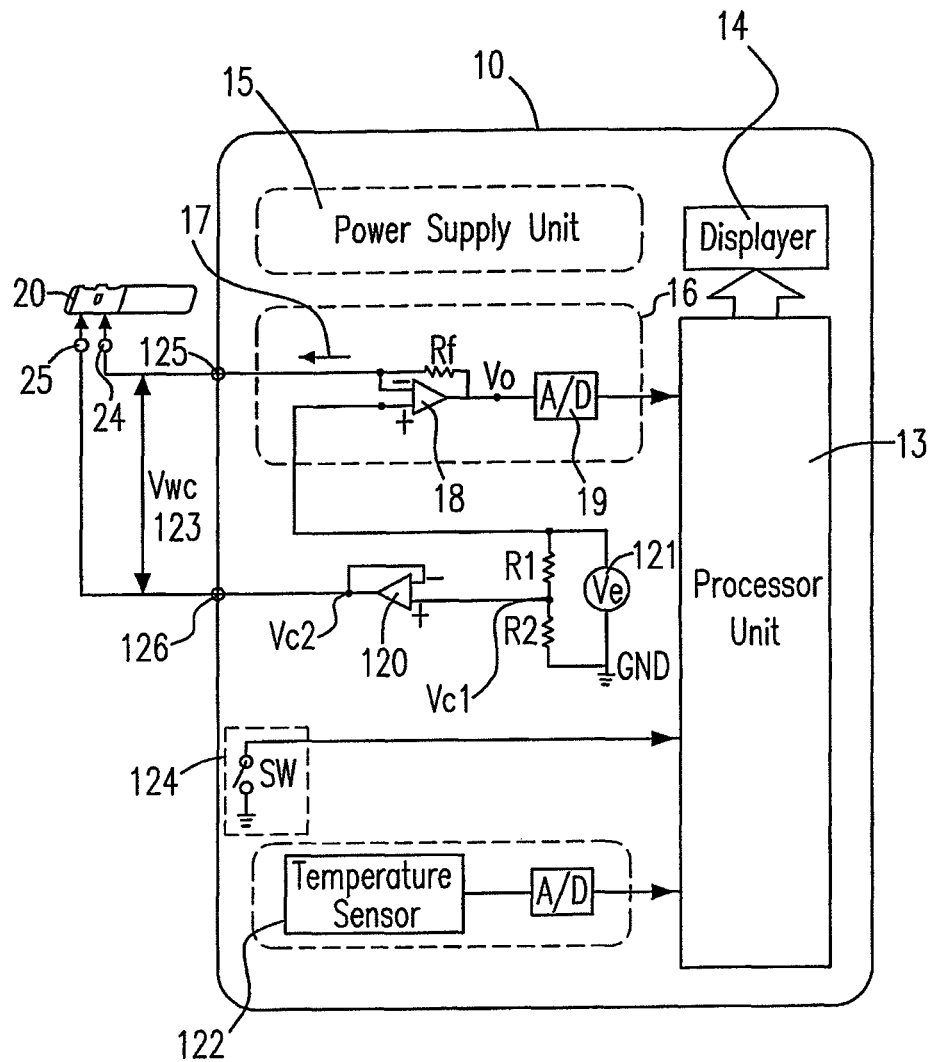
FIG. 2(C) shows the internal circuit configuration of the conventional meter used for the electrochemical test strip.

FIG. 2(C) shows the internal circuit configuration of conventional meter 10 used for the electrochemical test strip 20. The meter 10 has a processor unit 13, a displayer 14, a power supply unit 15, a current measurement unit 16, a current 17, a current-to-voltage converter 18, an analog-to-digital convertor 19, a current buffer 120, a voltage regulator 121, a temperature sensor 122, and a strip detecting unit 124 having a switch SW, wherein current-to-voltage converter 18 is configured in current measurement unit 16 and used for converting current 17 between contacts 24 and 25 into an analog voltage Vo (where Vo=I×Rf). The analog voltage Vo will be converted into an equivalent digital signal for being calculated by processor unit 13.

The divider formed by voltage regulator 121 and resistors R1 and R2 applies the voltage to contact Vc1, and current buffer 120 has a capability for driving high current and outputs a potential identical to that of contact Vc1 at contact Vc2. Under this situation, the potential of contact 125 is Vw, the potential of contact 126 is Vc, and an electrode voltage 123 is Vwc which is equal to the potential difference between Vw and Vc. Electrode voltage 123 is applied between contacts 125 and 126 respectively electrically connected to outputting contacts 24 and 25 of electrochemical test strip 20.

Please refer to FIGS. 3(A) to 3(E), wherein these figures illustrate the process that the sample flows into electrochemical test strip 20 and fully covers on electrodes 21 and 22.

FIGS. 3(A) to 3(E) are sectional drawings of electrochemical test strip 20 taken along the line A-A', wherein electrochemical test strip 20 has a channel 23, outputting contacts 24 and 25, a sample entrance 26, a cover 27, an air hole 28, a sample 29, a groove 210, upper surfaces of electrodes 211 and 212, through holes 213 and reagent 214, electrodes 21 and 22 are configured in through holes 213 in groove 210 of electrochemical test strip 20, and the respective areas of upper surfaces 211 and 212 are the same. Electrodes 21 and 22 are tightly surrounded by through holes 213 without any gap. The diameters of through holes 213 are designed to be slightly smaller than that of electrodes 21 or 22, so that electrodes 21 and 22 can be mechanically engaged in through holes 213.

Respective upper surfaces 211 and 212 of electrodes 21 and 22 form the working area of electrode, and respective sizes of upper surfaces 211 and 212 can be the same to or different from each other. The bottoms of electrodes 21 and 22 are outputting contacts 24 and 25 of electrochemical test strip 20, and outputting contacts 24 and 25 respectively connected to contacts 125 and 126 of meter 10 as shown in FIG. 2(C). Cover 27 is a hydrophilic one and has air hole 28 linked with the outside world. Cover 27 is further configured to cover groove 23 to form channel 23, wherein channel 23 is a capillary and defines a reaction region which is coated with reagent 214, and reagent 214 is covered on upper surfaces 211 and 212 of electrodes 21 and 22. Reagent 214 includes a known oxidative or reductive enzyme such as a glucose oxidase, an electron transport intermediate such as the potassium ferrocyanide (Fe(CN)63−), as well as some hydrophilic chemicals. The compositions of reagent 214 are the common means and not the focal point of the present invention. In addition, electrochemical test strip 20 provides sample entrance 26 for receiving sample 29, e.g. a drop of blood.

Figure 3A:
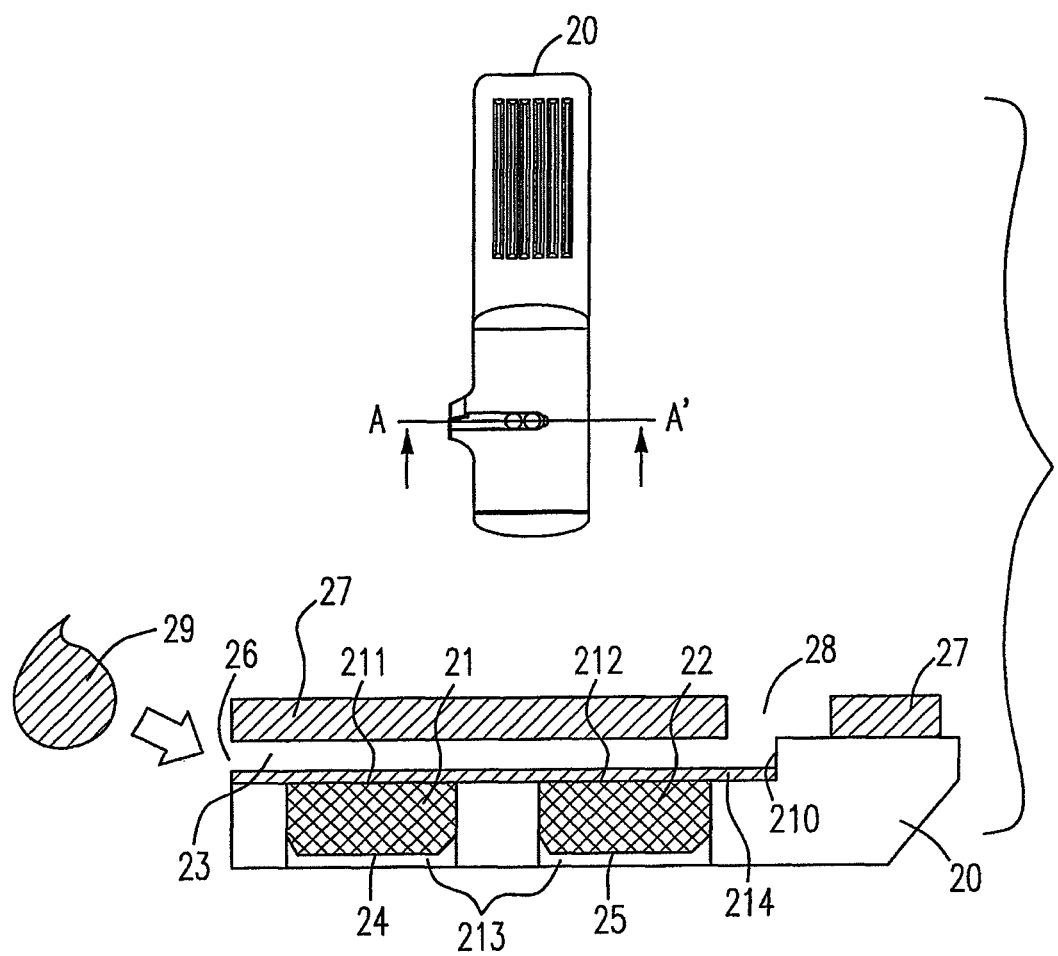
FIGS. 3(A), 3(B), 3(C), 3(D) and 3(E) are the cross-sectional diagrams of the electrochemical test strip and illustrate the process of the sample flowing into the electrochemical test strip.
Figure 3B:
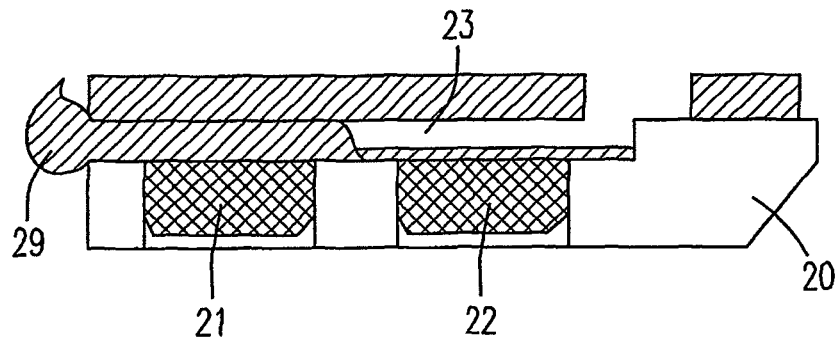
Figure 3C:
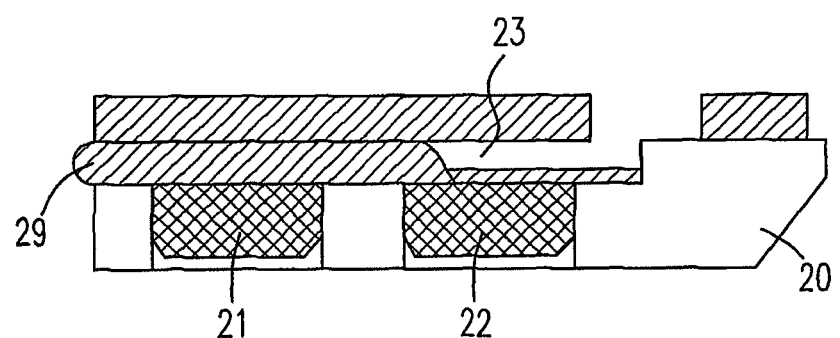
Figure 3D:
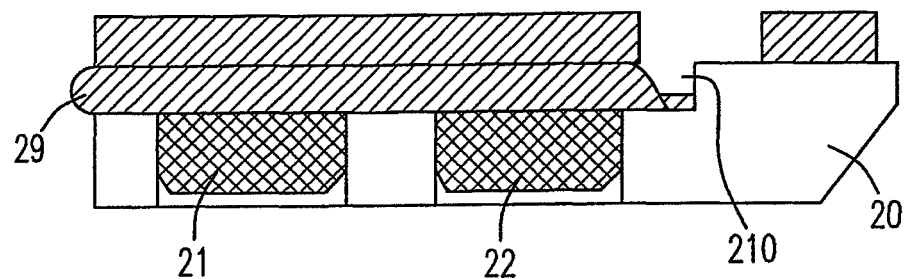
Figure 3E:
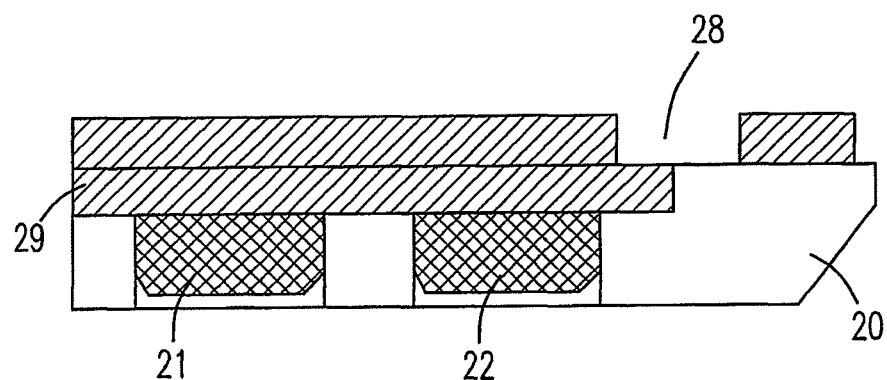

Please refer to FIG. 3(B). When placed on the opening of sample entrance 26, sample 29 will automatically be sucked into channel 23 due to the capillarity and/or the hydrophilic interaction. In addition, FIGS. 3(B) to 3(E) show the flowing process of sample 29 in channel 23. When sufficient sample 29 is dropped to the opening of sample entrance 26, sample 29 will flow along channel 23 as shown in FIGS. 3(C) and 3(D) until totally covers electrodes 21 and 22 as shown in FIG. 3(E), in the meanwhile the air in channel 23 is discharged through air hole 28.

As shown in FIG. 3(B), since sample 29 has not flowed onto electrode 22 yet, electrodes 22 and 23 are not conducted to each other and there is no sensing current generated therebetween although the situation shown in FIG. 3(B) belongs to those of sample detecting period 101 and the voltage has been applied to the electrodes.

In FIG. 3(C), sample 29 has been completely covered electrode 21 and partially covered electrode 22, and the sensing current will be generated between electrode 21 and 22 if the voltage is applied therebetween. At this time, meter 10 needs to estimate whether the value of the sensing current between electrodes 21 and 22 achieves sample detecting threshold 112, and the determination of sample detecting threshold 112 is very important.

From FIG. 3(C), it is apparently known that sample 29 does not fully cover electrode 22. Accordingly, if sample detecting threshold 112 is too low, the value of the sensing current between electrodes 21 and 22 under the situation shown in FIG. 3(C) will achieve sample detecting threshold 112 although sample 29 has not fully covered electrode 22 yet, so that meter 10 will misjudge and start the procedures of incubation period 105 and measurement period 106 and the concentration of the analyte in sample 29 obtained from such these procedures is incorrect. However, if sample detecting threshold 112 is too high, the value of the sensing current will not achieve sample detecting threshold 112 and meter 10 will not start the procedures of incubation period 105 and measurement period 106 even channel 23 is full of sample 29 as shown in FIG. 3(D) or 3(E). Moreover, the factors such as the hematocrit (HCT), or the contents of oxygen, glucose or lipid in the sample blood will interfere the sensing current, so that the value of the sensing current may be unable to achieve sample detecting threshold 112.

Therefore, the method which can correctively estimate whether the volume of sample in the reaction region is sufficient to obtain a correct sensing current is very important for such the meter.

Figure 4A:
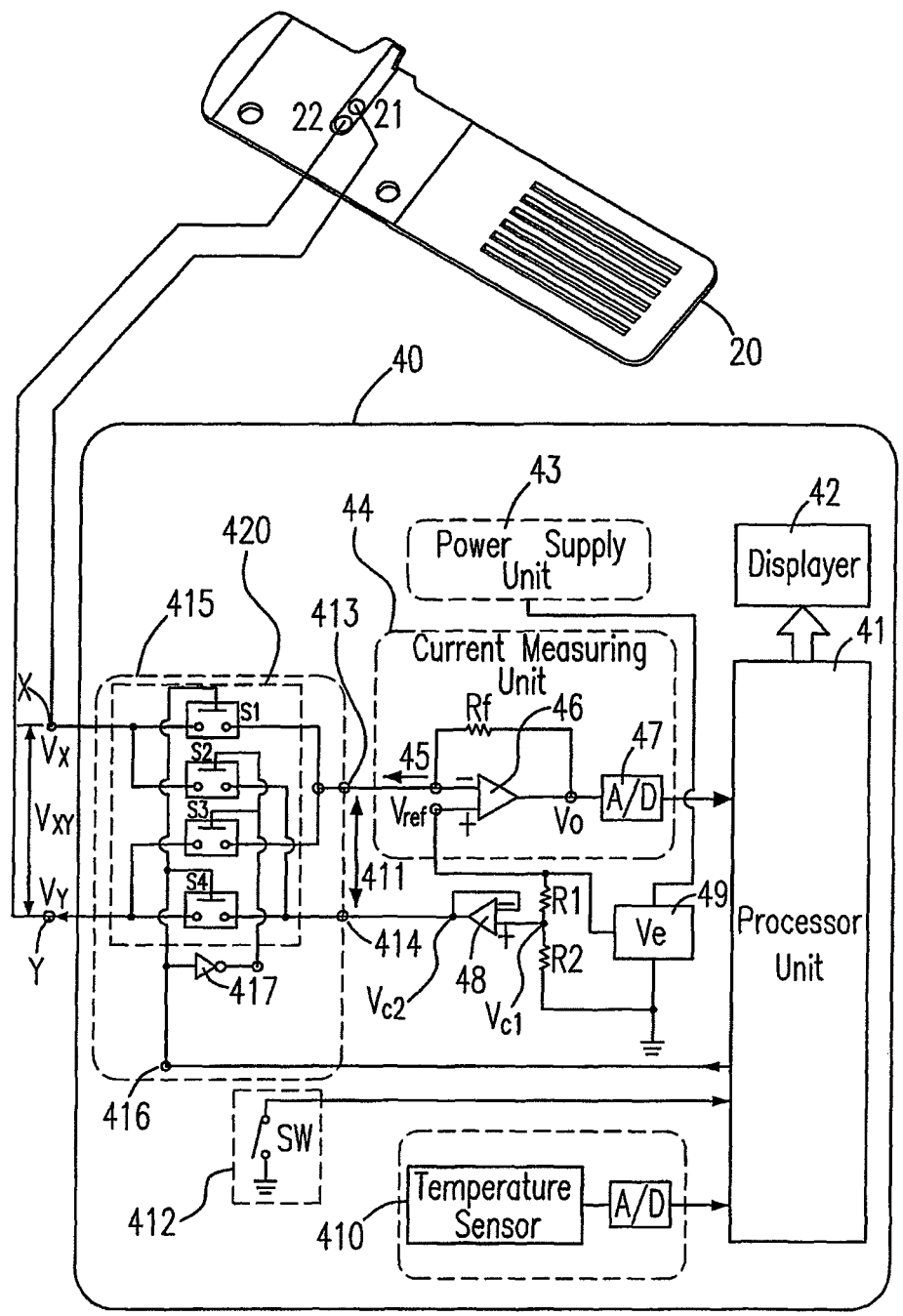
FIGS. 4(A), 4(B) and 4(C) show the internal circuit of the present meter suitable for the electrochemical test strip.

Please refer to FIG. 4(A), which shows the schematic diagram of the internal circuit of the present meter 40 suitable for electrochemical test strip 20. Although the present meter 40 shown in FIG. 4(A) and the following figures has an appearance identical to that of the conventional one, e.g. meter 20, the internal circuit and the measuring method of the present meter 40 are much advanced than that of the conventional one.

As for electrochemical test strip 20 in FIG. 4(A), it has been illustrated as above and will not repeat in the following passages.

FIG. 4(A) shows the internal configuration of meter 40. Meter 40 has a processor unit 41, a displayer 42, a power supply unit 43, a current measurement unit 44, a current 45, a current-to-voltage converter 46, an analog-to-digital convertor 47, a current buffer 48, a voltage regulator 49, a temperature sensor 410, a strip detecting unit 412 having a switch SW, and a voltage switching unit 415 having a switch set 420, wherein current-to-voltage converter 46 is configured in current measurement unit 44 and used for converting current 45 between electrodes 21 and 22 into an analog voltage Vo (where Vo=I×Rf). The analog voltage Vo will be converted into an equivalent digital signal for being calculated by processor unit 41.

In FIG. 4(A), the divider formed by voltage regulator 49 and resistors R1 and R2 applies the voltage to contact Vc1, and current buffer 48 has a capability for driving high current and outputs a potential identical to that of contact Vc1 at contact Vc2. Under this situation, the potential of contact 413 is Vw, the potential of contact 414 is Vc, and a working voltage 411 is Vwc which is equal to the potential difference between Vw and Vc and applied between contacts 413 and 414.

Switch set 420 has four switches S1, S2, S3 and S4, each of these four switches can be selected from a mechanical relay, an electronic type of analog switch and a MOSFET or a bipolar transistor to form a bridge switch for performing the switch. The voltage switching unit 415 includes a control contact 416 for receiving the digital control signal transmitted from processor unit 41, and controlling the turn on/off of switches S1 and S4 accordingly. If the digital control signal received by control contact 416 is 1, both of switches S1 and S4 will be turned on. On the contrary, if the digital control signal received by control contact 416 is 0, both of switches S1 and S4 will turn off.

Voltage switching unit 415 also includes an inventor 417 which is a basic component of the digital or the logic circuits and used to reverse the input signal. On the binary logic, if the input signal is 0, the output signal is 1; and when the input signal is 1, the output signal is 0. Such the principle is used to control the turn on/off of switches S2 and S3 and makes the time that switches S2 and S3 are turned off to be always different from that of switches S1 and S4. In other words, only one of switches S2 and S3, or switches S1 and S4 can be turned off (turned on) at a time.

Figure 4B:
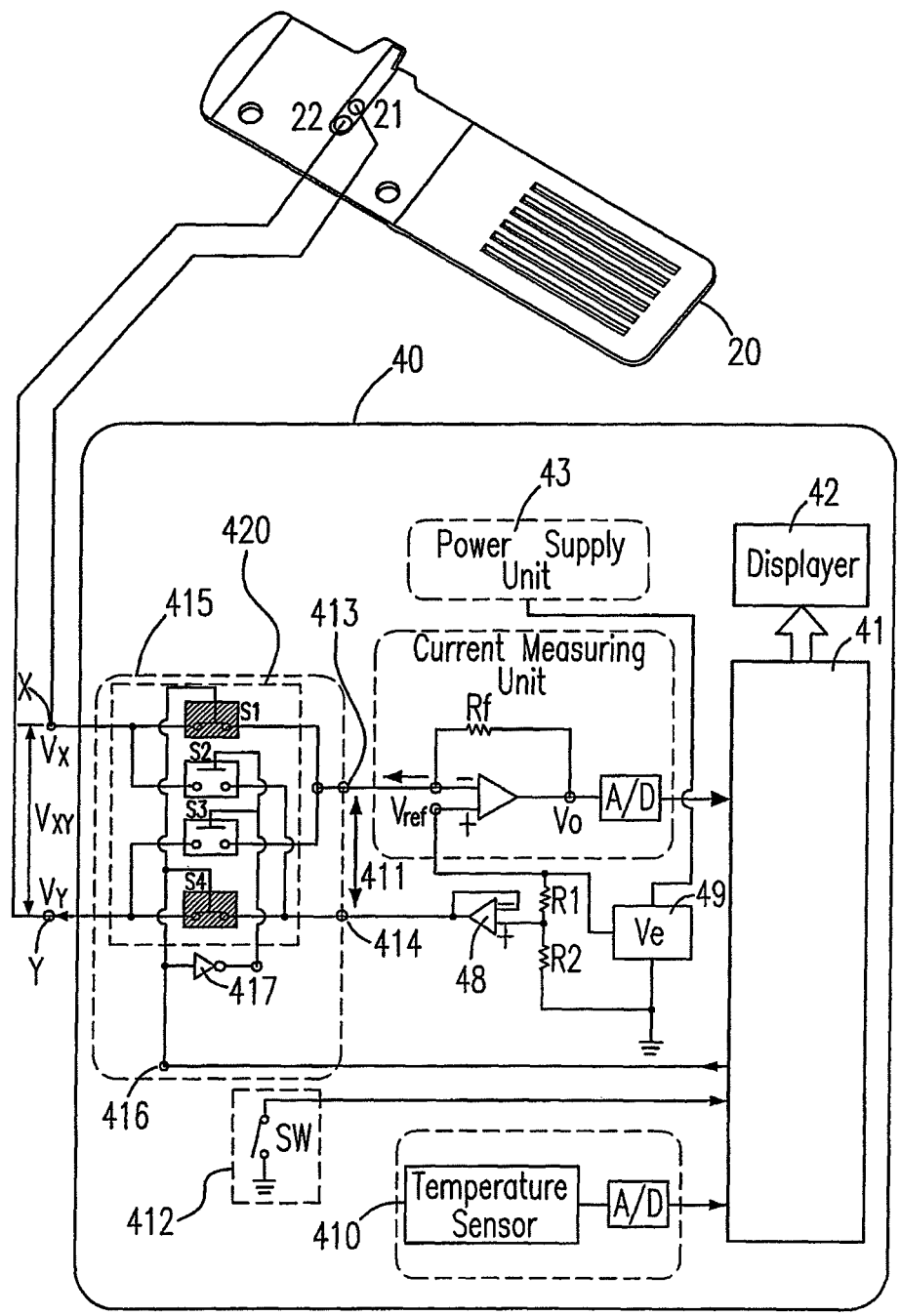
Figure 4C:
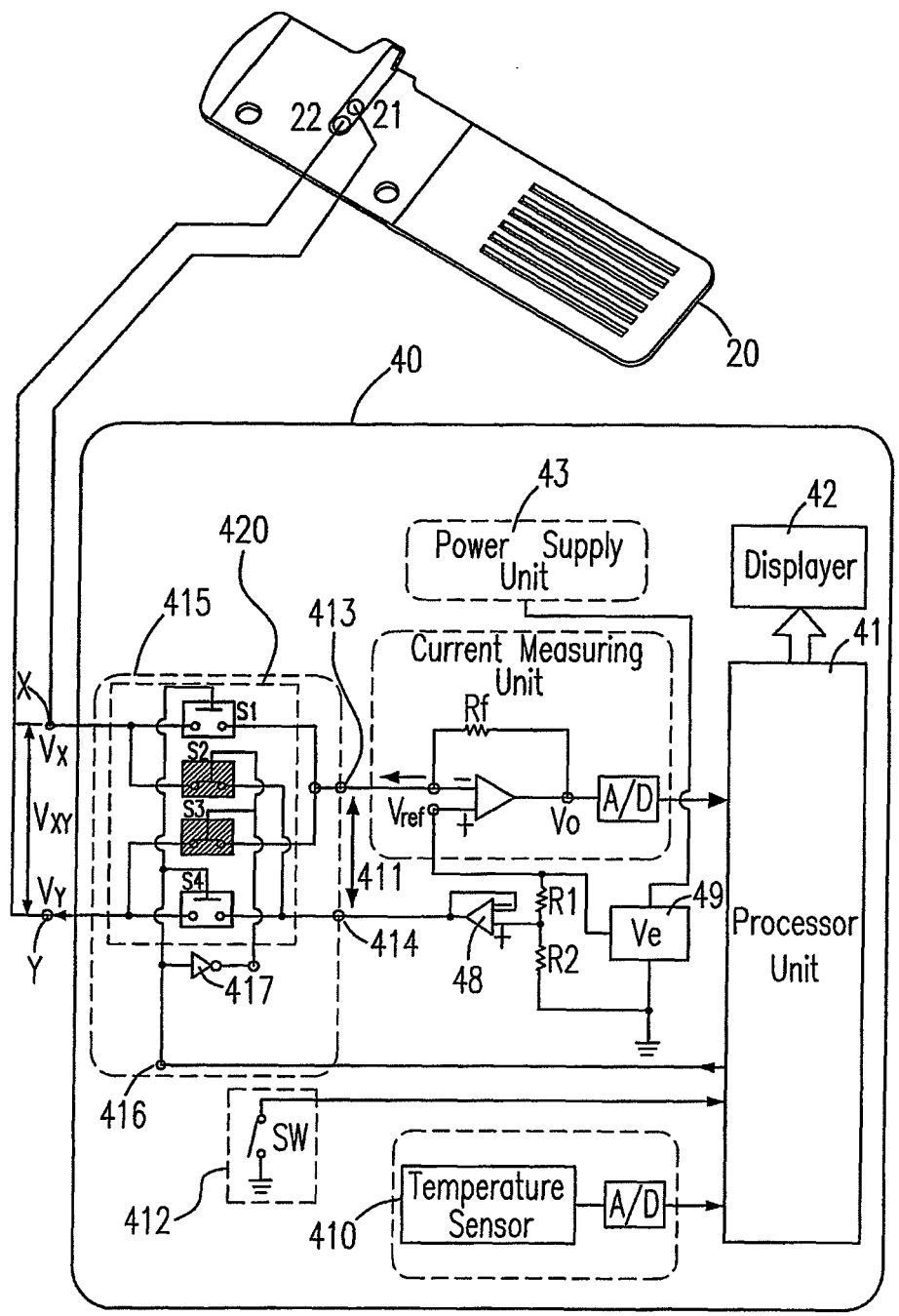

The control of voltage switching unit 415 is described as follows. As shown in FIG. 4(B), when processor unit 41 provides a digital signal 1 to control contact 416, the potentials of output X and contact 413 are the same since switch S1 is turned on, and the potentials of output X and contact 413 are Vx and Vw respectively; and the potentials of output Y and contact 414 are the same since switch S4 is turned on, and the potentials of output Y and contact 414 are Vy and Vc respectively.

Since Vx=Vw and Vy=Vc, the potential difference 411 between outputs X and Y equals to the potential difference Vwc between contacts 413 and 414. Presently, electrode 21 connected with output X is the working electrode because of Vx>Vy.

As shown in FIG. 4(B), when processor unit 41 provides a digital signal 0 to control contact 416, the potentials of output X and contact 414 are the same since switch S2 is turned on, and the potentials of output X and contact 414 are Vx and Vc respectively; and the potentials of output Y and contact 413 are the same since switch S3 is turned on, and the potentials of output Y and contact 413 are Vy and Vw respectively.

Since Vx=Vc and Vy=Vw, the potential difference 411 between outputs X and Y also equals the potential difference Vwc. Presently, electrode 22 connected with output Y is the working electrode because of Vx<Vy.

FIGS. 5(A) to 5(G) and 6(A) to 6(I) show an embodiment of the present method, wherein FIGS. 5(A) to 5(G) are partially amplified diagrams of electrochemical test strip 20. The procedures of the present method are described as follows.

(1) Inserting electrochemical test strip 20 into the slot of meter 40 to turn on switch 412 so as to cause processor unit 41 circularly transmitting digital signals of 1 and 0 to control contact 416. Presently, the DC voltages of outputs X and Y are shown as FIGS. 6(A) and 6(C) respectively.

(2) Then, display 42 shows a request for the supply of sample 29, typically a blood drop sample.

Figure 5A:
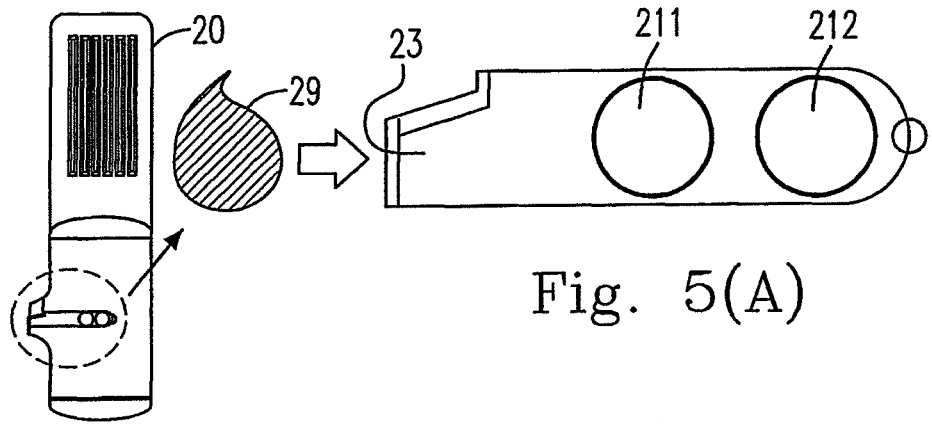
FIGS. 5(A), 5(B), 5(C), 5(D), 5(E), 5(F) and 5(G) are partially amplified diagrams of the electrochemical test strip and illustrate the process of the sample flowing into the electrochemical test strip.

(3) When placed on the opening of sample entrance 26 (referring to FIG. 3(A) or 5(A)), sample 29 will automatically be sucked into channel 23 due to the capillarity and/or the hydrophilic interaction. FIGS. 5(B) to 5(G) show the flow of sample 29 in channel 23.

Figure 5B:
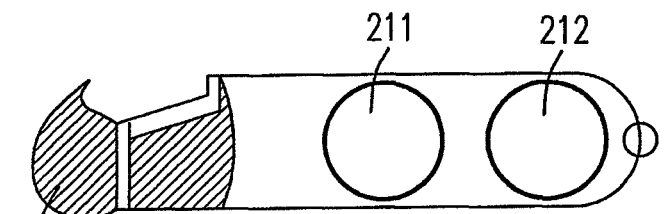
Figure 5C:
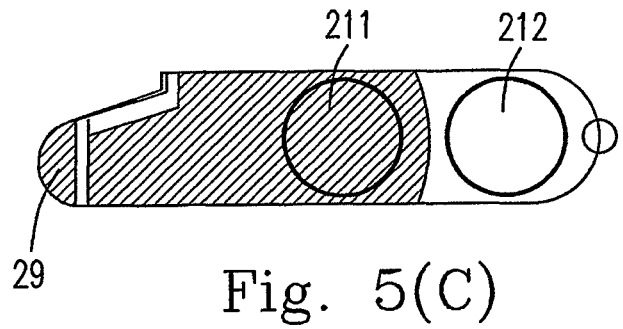
Figure 5D:
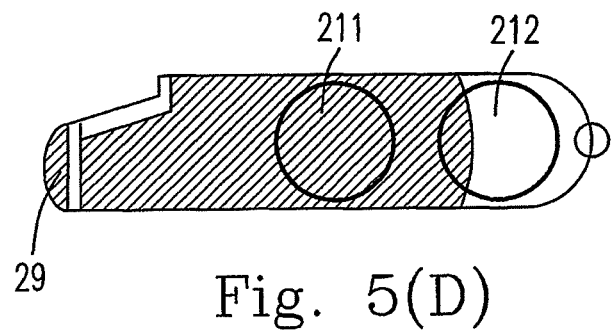

(4) From the time shown in FIG. 5(D), processor unit 41 starts receiving the sensing current generated between the electrodes of electrochemical test strip 20.

Figure 6A:
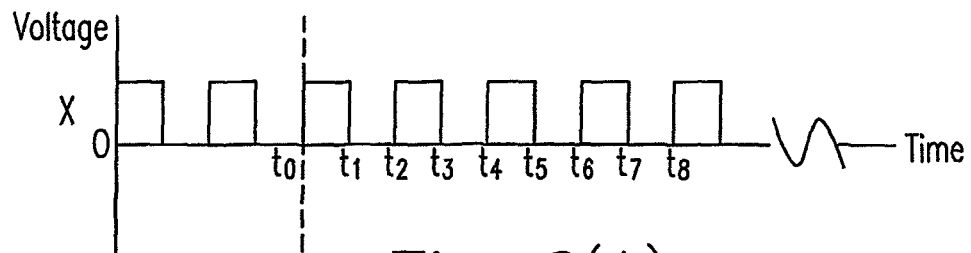
FIGS. 6(A), 6(B), 6(C) and 6(D) show the voltage and the current generated during the electrochemical reaction occurring on the electrochemical test strip, and 6(E), 6(F), 6(G) 6(H) and 6(I) are the cyclic voltammograms during the electrochemical reaction occurring on the electrochemical test strip.
Figure 6B:
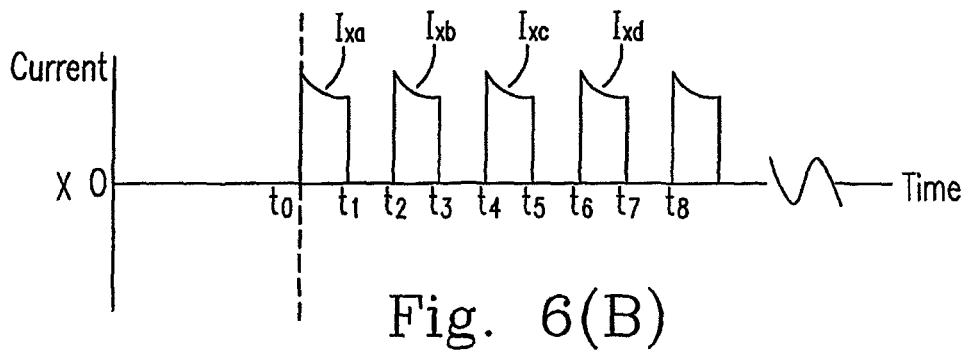
Figure 6C:
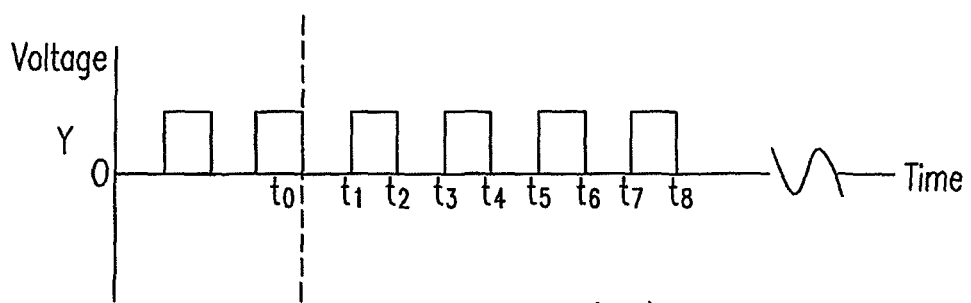

(A) When the time is 0~to, the flow of sample of 29 is shown as FIGS. 5(B) and 5(C), and the sensing currents respectively received by outputs X and Y are shown as FIGS. 6(B) and 6(C). Presently, sample 29 has not flowed onto upper surface 212 of electrode so that there is no sensing current generated, and the corresponding cyclic voltammograms is shown as FIG. 6(E).

Figure 6D:
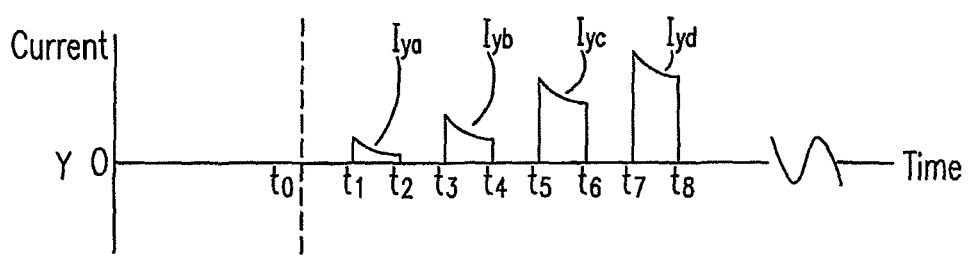
Figure 6E:
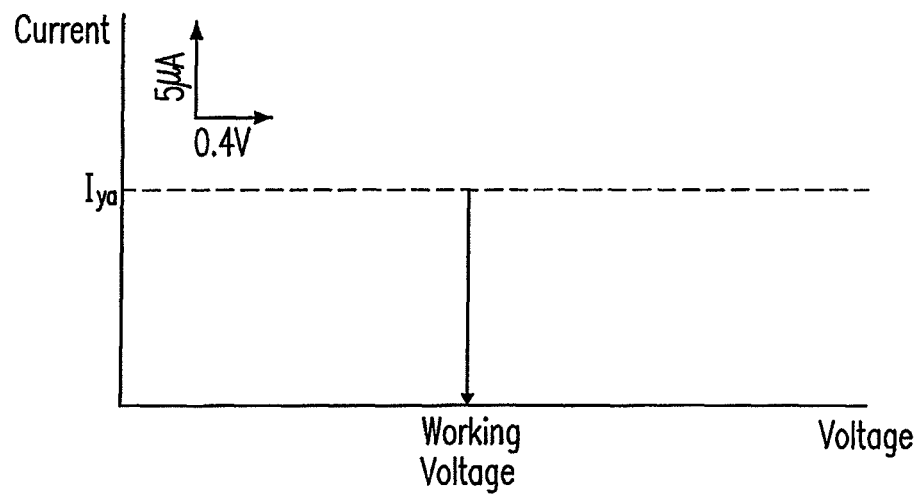
Figure 6F:
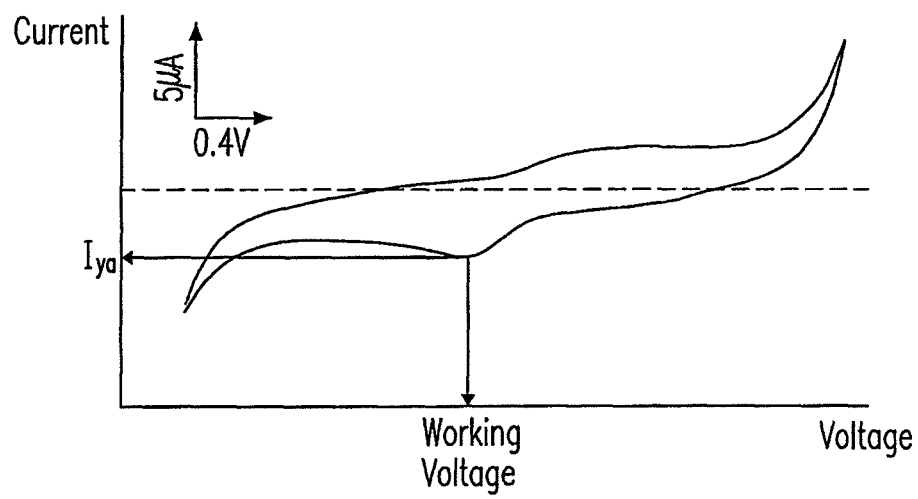
Figure 6G:
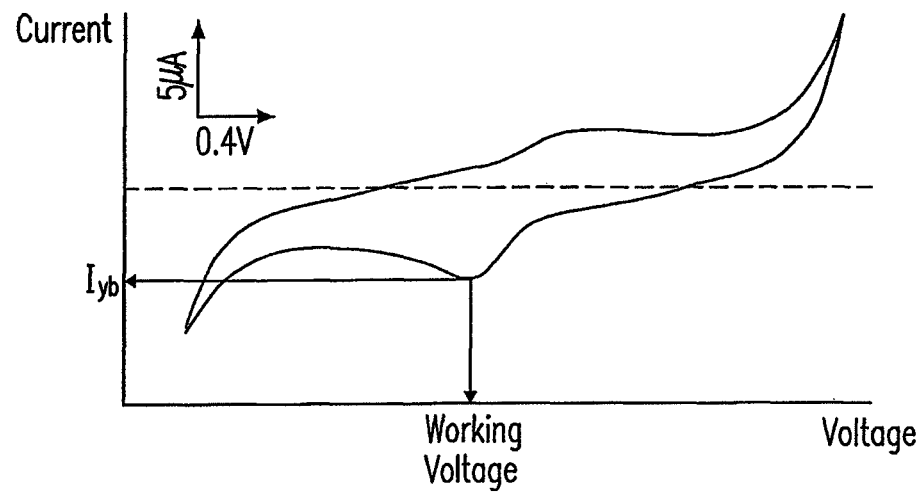
Figure 6H:
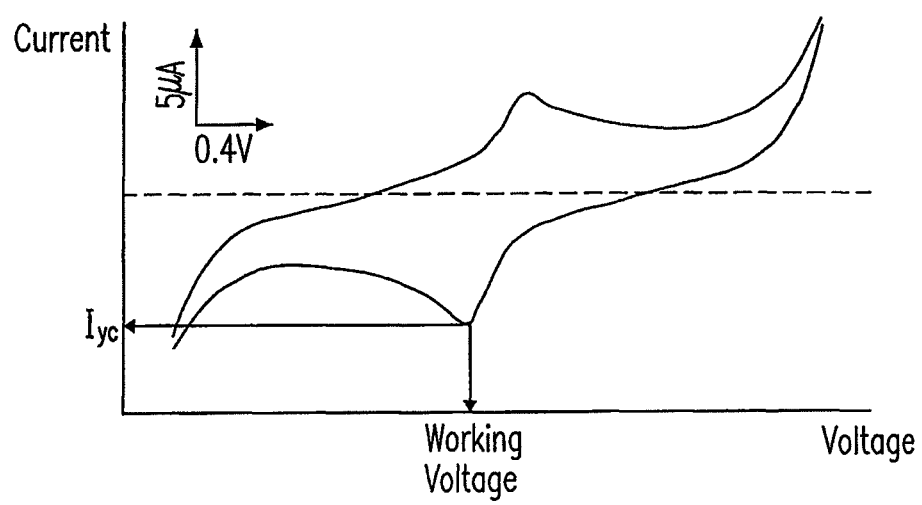
Figure 6I:
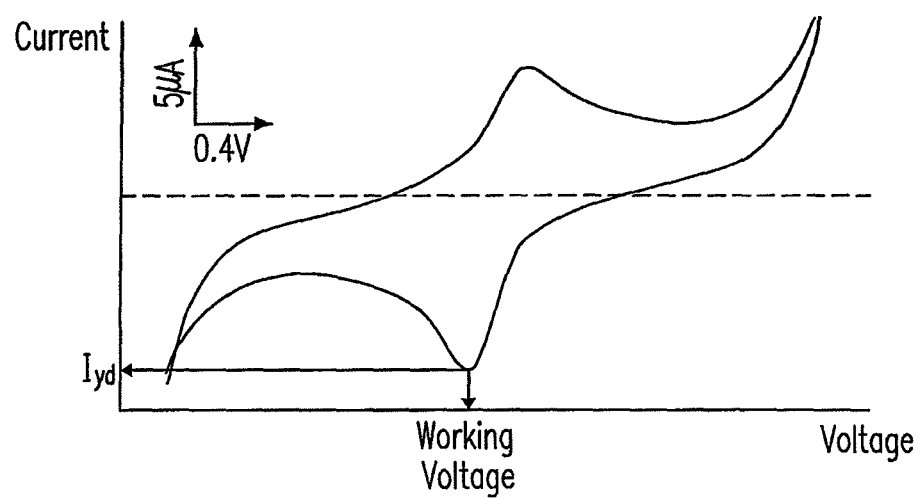

(B) When the time is to~t2, sample 29 has partially covered electrode surface 212 as shown in FIG. 5(D), and the sensing current is initially generated as shown in FIGS. 6(B) and 6(D), wherein the sensing current received by output X has a value of Ixa, and the sensing current received by output Y has a value of Iya at this time. Since sample 29 has completely covered upper surface 211, but only partially covers upper surface 212, so that Ixa is much greater than Iya. When the time is to~t1, the working voltage is Vwc, the working electrode is electrode 21 and the area of the working electrode is the whole area of upper surface 211. When the time is t1~t2, the working voltage is still Vwc, the working electrode is electrode 22 and the area of the working electrode is the area of upper surface 212 covered by sample 29. According to the Cottrell Equation, since the sensing current is proportional to the area of the working electrode, the sensing current Iya measured during t1~t2 is smaller than that (Ixa) measured during to~t1. In addition, the cyclic voltammograms corresponding to t1~t2 is shown as FIG. 6(F).

Figure 5E:
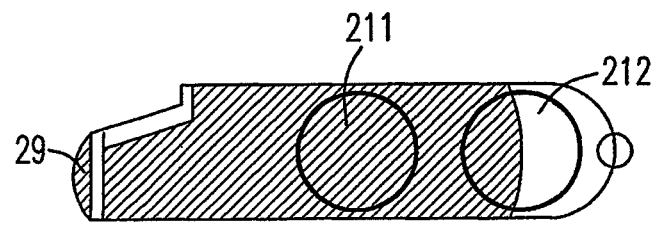

(C) When the time is t2~t4, sample 29 has more covered electrode surface 212 as shown in FIG. 5(E), the sensing current received by output X has a value of Ixb, and the sensing current received by output Y has a value of Iyb at this time, wherein Ixb is slightly smaller than Ixa due to the consumption of current during to~t2, but such the difference between Ixb and Ixa is so minor and can be ignored. In addition, Iyb is greater than Iya since the area of upper surface 212 covered by sample 29 as shown in FIG. 5(E) is greater than that shown in FIG. 5(D). Presently, the corresponding cyclic voltammograms is shown as FIG. 6(G).

Figure 5F:
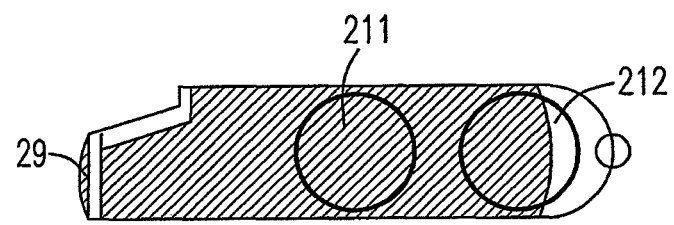

(D) When the time is t4~t6, sample 29 has further more covered electrode surface 212 as shown in FIG. 5(F), the sensing current received by output X has a value of Ixc, and the sensing current received by output Y has a value of Iyc at this time, wherein Ixc is approximately equals to Ixb, and Iyc is greater than Iyb since the area of upper surface 212 covered by sample 29 as shown in FIG. 5(F) is greater than that shown in FIG. 5(E). Presently, the corresponding cyclic voltammograms is shown as FIG. 6(H).

Figure 5G:
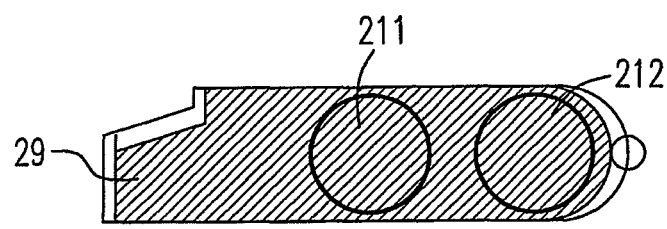

(E) When the time t6~t8, sample 29 has totally covered electrode surface 212 as shown in FIG. 5(G), the sensing current received by output X has a value of Ixd, and the sensing current received by output Y has a value of Iyd at this time, wherein Ixd is approximately equals to Ixc, Iyd is greater than Iyc, and Ixd is approximately equals to Iyd since upper surface 212 has been totally covered by sample 29 as shown in FIG. 5(G) and the respective areas of upper surfaces 211 and 212 are the same. Presently, the corresponding cyclic voltammograms is shown as FIG. 6(I).

(5) Upon processor unit 41 receives the sensing current, it begins to calculate and estimate whether sample 29 in the reaction region is sufficient. Such the estimation can be preformed via several ways. For example, processor unit 41 continuously receives and operates the sensing currents received from outputs X and Y during a specific period, and then starts the next step, i.e. starts incubation period 105, upon the ratio of Iy (the sensing current received from output Y) over Ix (the sensing current received from output X) greater than or equal to a first predetermined value, or the ratio of Ix/Iy smaller than or equal to a second predetermined value; if the ratio of Iy/Ix (or Ix/Iy) can not achieve the above-mentioned predetermined value after a predefined period, displayer 42 will show the message of the insufficiency of the volume of sample (i.e. volume of blood). In another way, processor unit 41 respectively sums up the received Ixs and the received Iys, and then starts the next step upon the ratio of the sum of received Ixs over the sum of received Iys (Ixs/Iys) is not smaller than (or not greater than) a predetermined value; if the ratio of Ixs/Iys (or Iys/Ixs) can not achieve the above-mentioned predetermined value after a predefined period, displayer 42 will also show the message of the insufficiency of the volume of sample.

(6) If processor unit 41 estimates that sample 29 in the reaction region is sufficient, the standard procedures from incubation period 105 to measurement period 106 will be performed to obtain a correct value of sensing current. Processor unit 41 will operates this correct value of sensing current to obtain the concentration of the target analyte in sample 29, and displayer 42 will show the value of the concentration of the target analyte.

The preferable range of ratio for estimating the distribution of sample on the electrodes is obtained from the experiments of which samples having various volumes are used. The details of these experiments are described as follows.

(1) A test strip being suitable for a meter is provided, wherein the sufficient volume of sample for filling the reaction region of the test strip is 0.7 µL, the test strip has a first and a second electrodes, and the area of the first electrode is smaller than that of the second electrode.

(2) Then, the samples is driven to flow from the first electrode to the second electrode, wherein the sample has various volumes from 0.3 µL to 0.8 µL and such the flowing process of sample are performed several times.

(3) Applying a first DC voltage of 0.1V between the first and the second electrodes for a first duration of 20 ms to cause the potential of the first electrode higher than that of the second electrode. The first Cottrell current generated during the first duration is measured and recorded.

(4) The first DC voltage is removed for a first removing duration of 20 ms. Additionally, the removing duration can be 0 ms to 50 ms upon requests.

(5) Applying a second DC voltage of 0.1V between the first and the second electrodes for a second duration of 20 ms to cause the potential of the second electrode higher than that of the first electrode. The second Cottrell current generated during the second duration is measured and recorded. Additionally, the first and the second durations can be the same or different from each other, and the range of the two durations is 3 ms to 2 s upon requests.

(6) The ratio of the first Cottrell current over the second Cottrell current is calculated.

Every sample having various volumes are processed according to the above-mentioned steps (1) to (6) for more than ten times, where the ranges of ratios for each sample and the coefficient of variation (CV %) of the first Cottrell current are recorded as shown in Table 1.

| Volume of sample | Average value of the first Cottrell currents (µA) | Coefficient of variation (CV %) of the first Cottrell current | Range of ratio of the first Cottrell current/the second Cottrell current | Range of ratio of the second Cottrell current/the first Cottrell current |
|---|---|---|---|---|
| 0.3 µL | N/A | N/A | N/A | N/A |
| 0.4 µL | 2.89 | 11 | 0.1-0.5 | 2.0-10 |
| 0.45 µL | 3.55 | 4.52 | 0.3-0.6 | 1.6-3.3 |
| 0.5 µL | 3.85 | 3.82 | 0.6-0.9 | 1.1-1.6 |
| 0.6 µL | 4.00 | 2.14 | 1.0-1.4 | 0.7-1.0 |
| 0.7 µL (volume for filling the reaction region) | 3.95 | 1.39 | 1.3-1.6 | 0.6-0.8 |
| 0.8 µL | 3.98 | 2.05 | 1.3-1.7 | 0.6-0.8 |

Based on Table 1, it can be realized if the sample volume is too small, e.g. 0.3 µL, the Cottrell current is unable to be generated since the sample volume of 0.3 µL is insufficient for the sample flowing from the first electrode to contact the second electrode. Although the first Cottrell current can be obtained when the sample volume is 0.4 µL, the CV % is poor (where CV %>10%). When the sample volume raises to 0.45 µL to 0.8 µL, the CV % of the first Cottrell current is preferable and acceptable (where CV %<5%), and the ranges of ratio of the first Cottrell current/the second Cottrell current, and the second Cottrell current/the first Cottrell current are 0.3 to 1.7 and 0.6 to 3.3 respectively. In other words, it reveals that the sample has a preferable distribution/cover within the reaction region of the test strip if the ratio of the Cottrell currents is between 0.3 to 3.3.

Figure 7A:
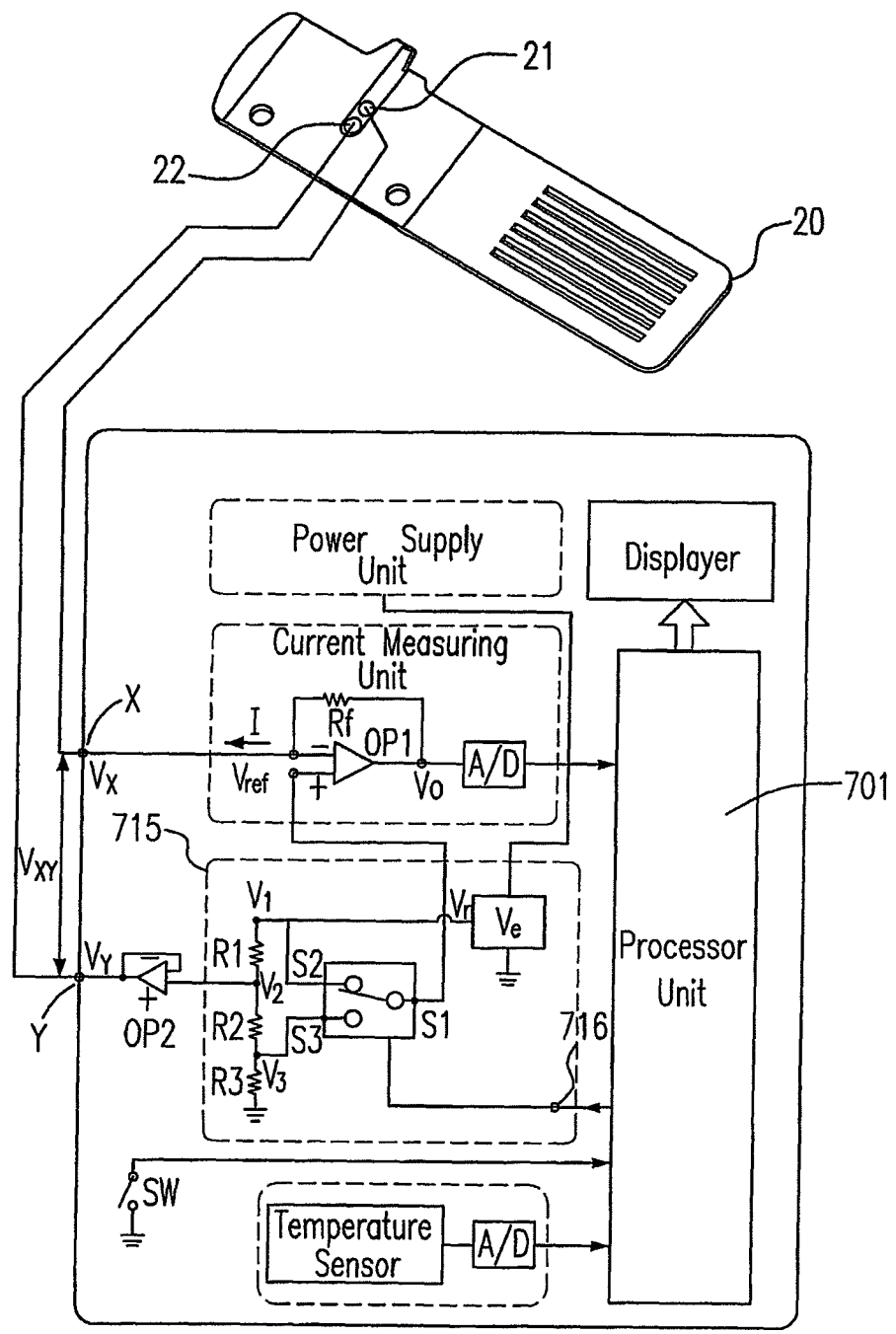
FIGS. 7(A) and 7(B) show the internal circuit of another embodiment of the present meter.
Figure 7B:
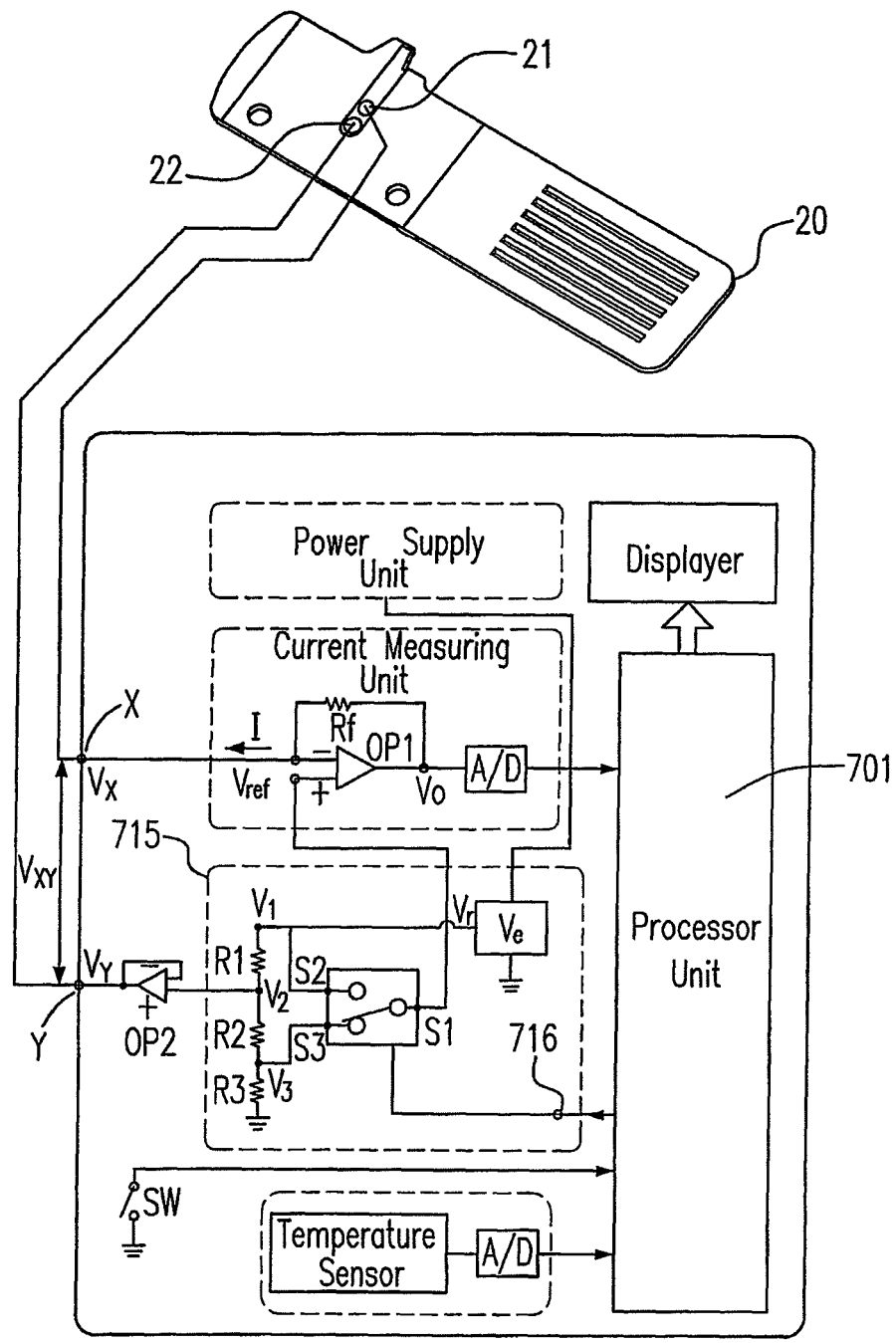

FIGS. 7(A) and 7(B) show another embodiment of the present invention, where the configuration of voltage switching unit 715 is different from that of voltage switching unit 415 as shown in FIG. 4(B). Voltage switching unit 715 receives the control signals transmitted from processor unit 701 by a control contact 716 and switches the switches S1, S2 and S3 accordingly, which is described as follows.

When S1 and S2 is connected as shown in FIG. 7(A), that:
$Vx=Vref=V1=Vr$;
$Vy=V2=[(R2+R3)/(R1+R2+R3)] Vr$; and
$Vxy=Vx-Vy=Vr-[(R2+R3)/(R1+R2+R3)] Vr=[R1/(R1+R2+R3)] Vr$. Therefore, $Vx>Vy$ and electrode 21 connected to output X is the working electrode at this time.

When S1 and S3 is connected as shown in FIG. 7(B), that:
$Vx=V3=[R3/(R1+R2+R3)] Vr$;
$Vy=V2=[(R2+R3)/(R1+R2+R3)] Vr$; and
$Vxy=Vx-Vy=[R3/(R1+R2+R3)] Vr-[(R2+R3)/(R1+R2+R3)] Vr=[-R2/(R1+R2+R3)] Vr$. Therefore, $Vy>Vx$ and electrode 22 connected to output Y is the working electrode at this time.

If R1 is defined as the same as R2, the voltage differences Vxy under the mode of S1 connected to S2 and the voltage under the mode of S1 connected to S3 have the same value and the respective polarities thereof are inversed.

Based on this embodiment of switches among switches S1, S2 and S3, the value of sensing current shown in FIGS. 6(A) to 6(I) can also be obtained accordingly so as to estimate whether the sample volume is sufficient for the test strip.

Figure 8:
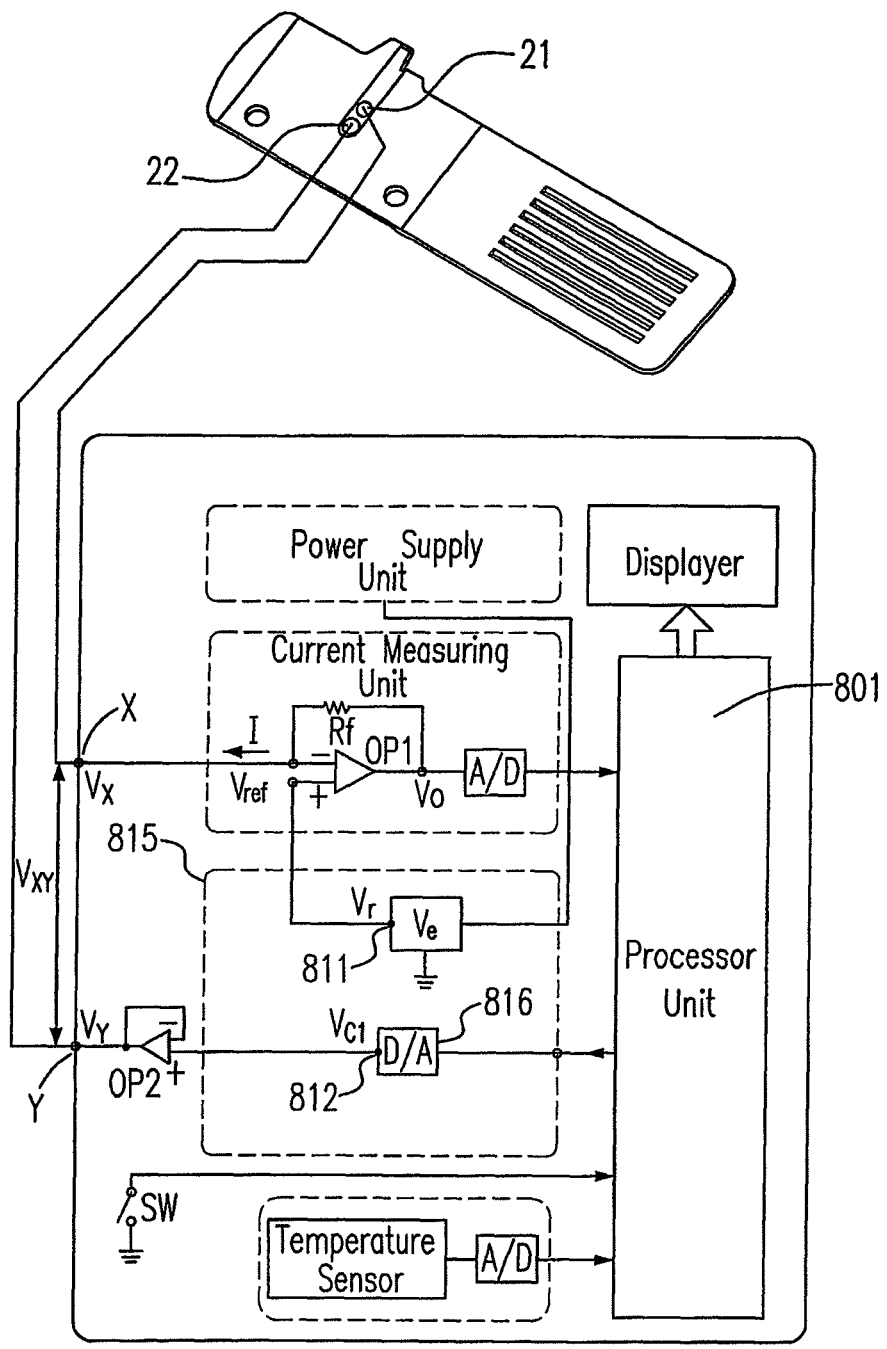
FIG. 8 shows the internal circuit of another embodiment of the present meter.

FIG. 8 shows another embodiment of the present invention, where the configuration of voltage switching unit 815 is different from those of voltage switching units 415 and 715. In the embodiment shown in FIG. 8, Vx (voltage on output X) equals to Vr (voltage on contact 811), and is a constant voltage, and voltage switching unit 815 receives the control signals transmitted from processor unit 801, converts the control signal into the analog voltage by a digital-to-analog voltage converter 816, provides the analog voltage Vc1 to contact 812 and enhances the output driving force of the current by a current buffer OP2. At this time, Vy equals to Vc1 and Vy is adjusted by the control signals of processor unit 801 to achieve the switch of the voltage. The above descriptions are further elaborated as follows.

The absolute value of the working voltage Vxy applied between outputs X and Y is predetermined as Q.

Processor unit 801 transmits the digital control signals to adjust Vc1 at a first time, so that:
Vc1=Vy=Vx−Q; and
Vxy=Vx−Vy=Vx−(Vx−Q)=Q. Therefore, Vx>Vy and electrode 21 connected to output X is the working electrode at this first time.

Processor unit 801 transmits the digital control signals to adjust Vc1 at a second time, so that:
Vc1=Vy=Vx+Q; and
Vxy=Vx−Vy=Vx−(Vx+Q)=−Q. Therefore, Vy>Vx and electrode 22 connected to output Y is the working electrode at this second time.

Based on this embodiment that Vc1 is adjusted and switched according to the digital control signals transmitted from processor unit 801 at the first and the second times, and the value of sensing current shown in FIGS. 6(A) to 6(I) can also be obtained accordingly so as to estimate whether the sample volume is sufficient for the test strip.

Through the present invention, when sample enters into sample entrance 26 and processor units 41, 701 and 801 receives a sensing current, the sensing current is estimated whether achieves sample detecting threshold 112. If the sensing current achieves sample detecting threshold 112, the standard procedures from incubation period 105 to measurement period 106 are performed. The switch of voltage as mentioned in the above embodiments can be performed at any time within incubation period 105 to measurement period 106, and Ix and Iy are obtained for further operating by processor units 41, 701 and 801. The effectiveness of the operating results at or after the end of measurement period is further confirmed based on the steps disclosed in the above embodiments. In other words, the present method can be performed at any time within sample detecting period 101, incubation period 105 and measurement period 106 to estimate the effectiveness of the operating results at or after the end of measurement period.

Figure 9A:
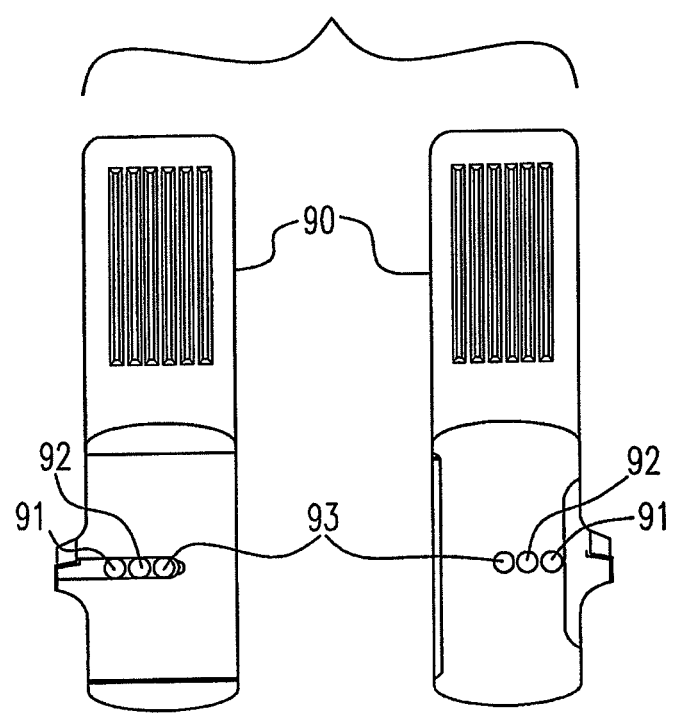
FIG. 9(A) is another embodiment of the electrochemical test strip.
Figure 9B:
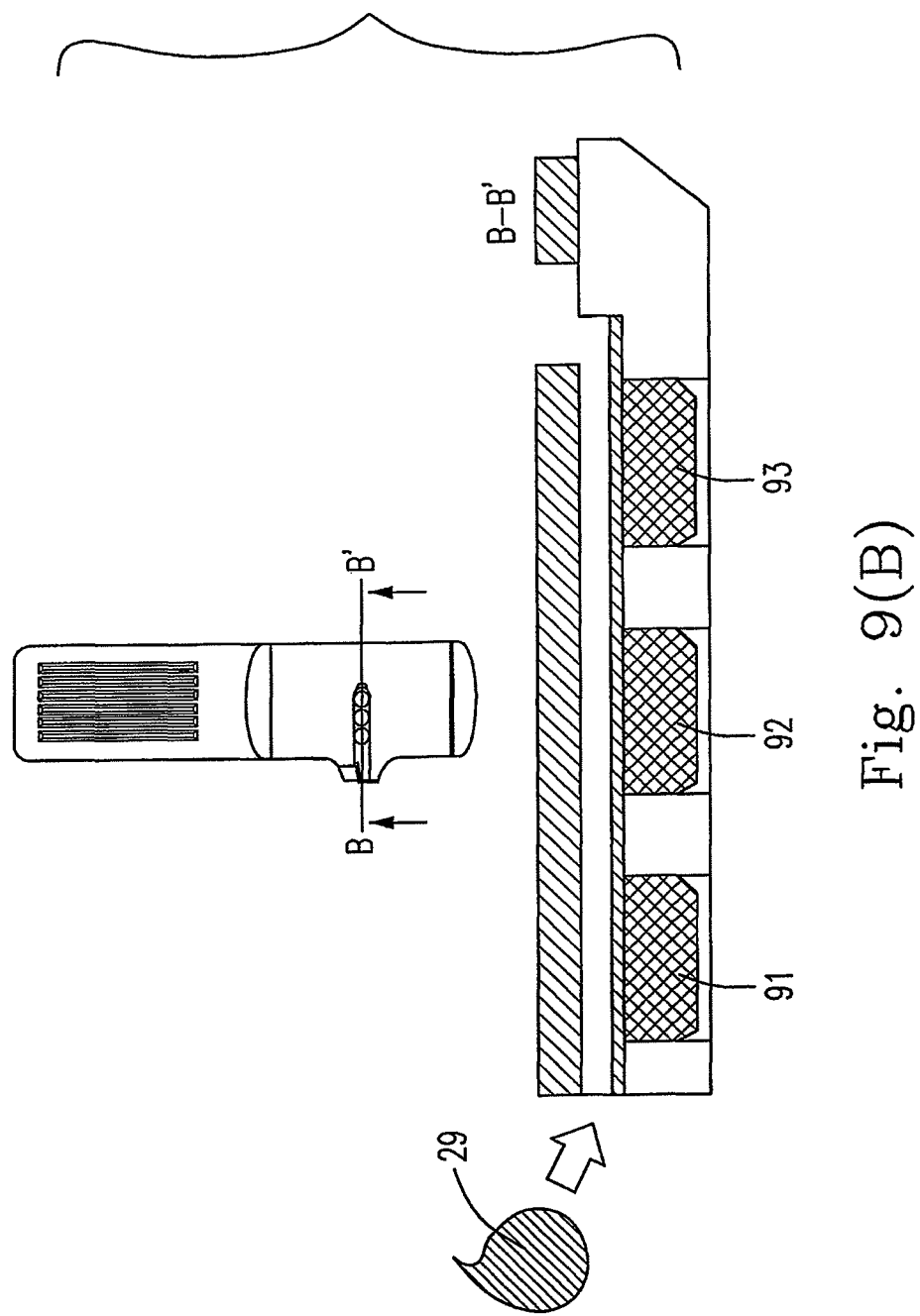
FIG. 9(B) is a sectional drawing of the electrochemical test strip shown in FIG. 9(A).

Please refer to FIGS. 9(A) and 9(B), which show another embodiment of electrochemical test strip shown in FIGS. 2(B), and 9(B) is a sectional drawing of electrochemical test strip 90 taken along the line B-B'. Electrochemical test strip 90 has two electrodes 91 and 92 and a reference electrode 93, wherein each of electrodes 91 and 92 will be the working electrode at a specific time when the voltage switching unit (415, 715 or 815) operates as above-mentioned and the Cottrell current is generated accordingly. When the meter estimates the blood sample volume in electrochemical test strip 90 as sufficient, reference electrode 93 assists in further stabilizing predetermined voltage 107 applied to electrodes 91 and 92 during measurement period 106 to obtain a more accurate sensing current.

Figure 10A:
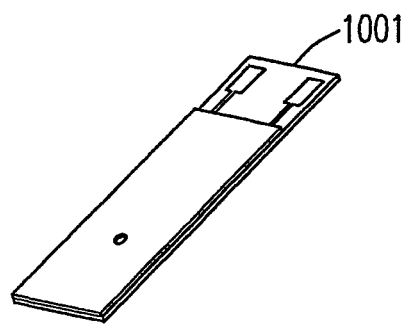
FIG. 10(A) is another embodiment of the electrochemical test strip.
Figure 10B:
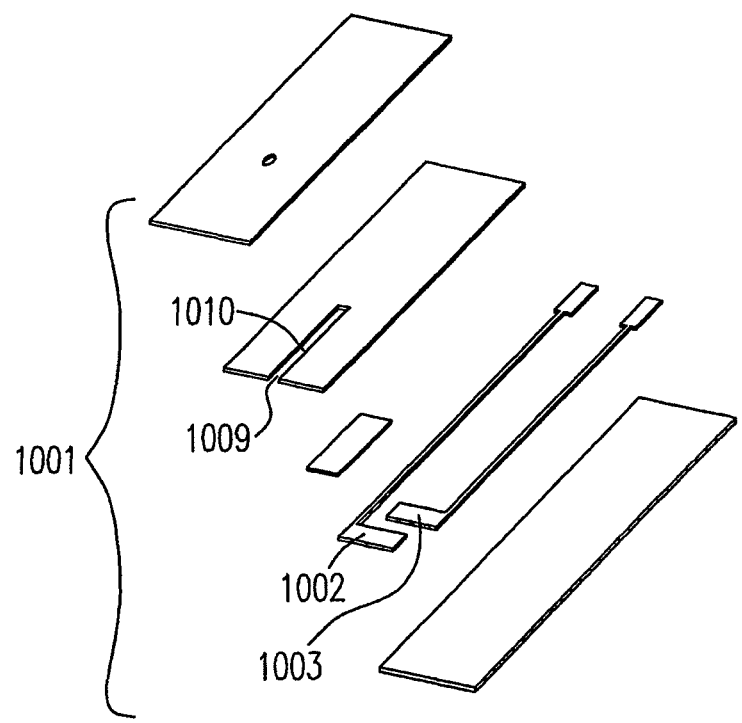
FIG. 10(B) is an explosion drawing of the electrochemical test strip shown in FIG. 10(A), and FIGS. 10(C) and 10(D) are the sectional drawings of the electrochemical test strip shown in FIG. 10(A) and illustrate the process of the sample flowing into the electrochemical test strip.
Figure 10C:
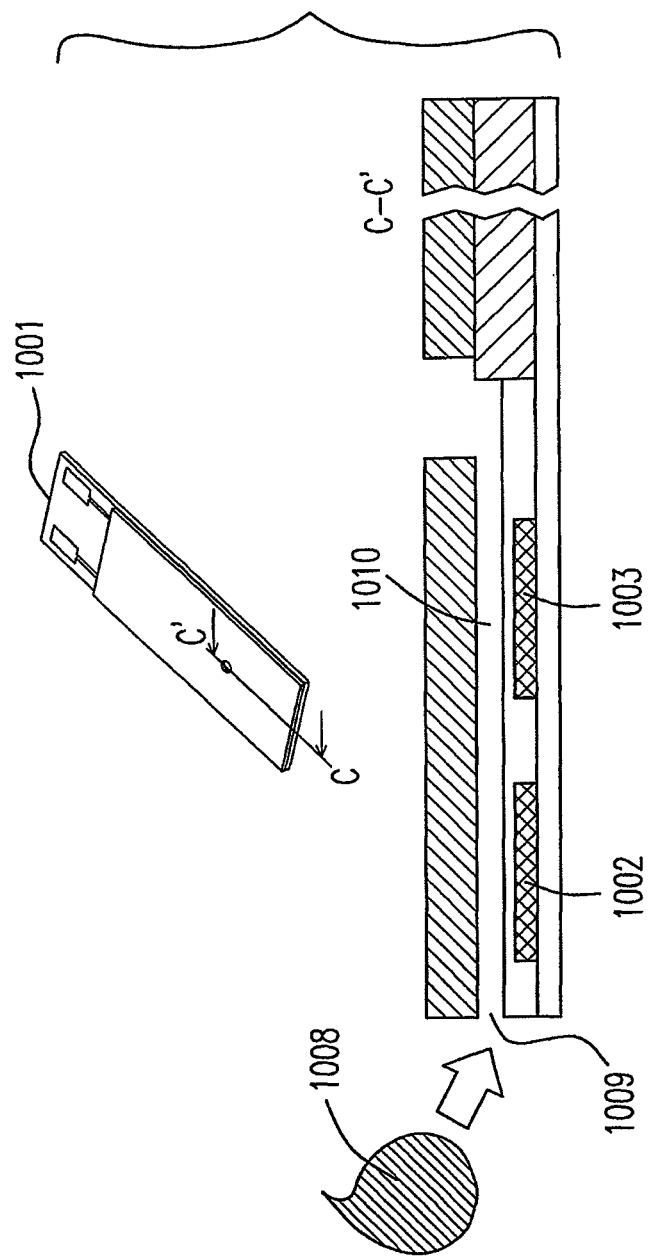
Figure 10D:
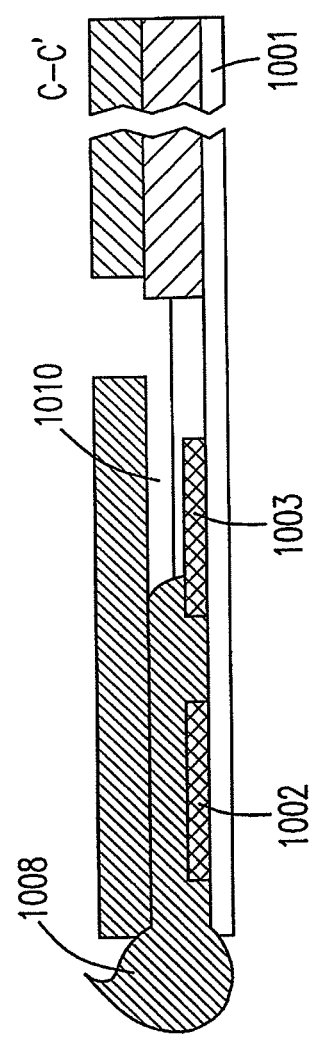
Figure 11A:
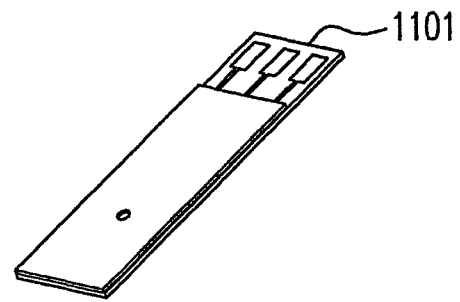
FIG. 11(A) is another embodiment of the electrochemical test strip.
Figure 11B:
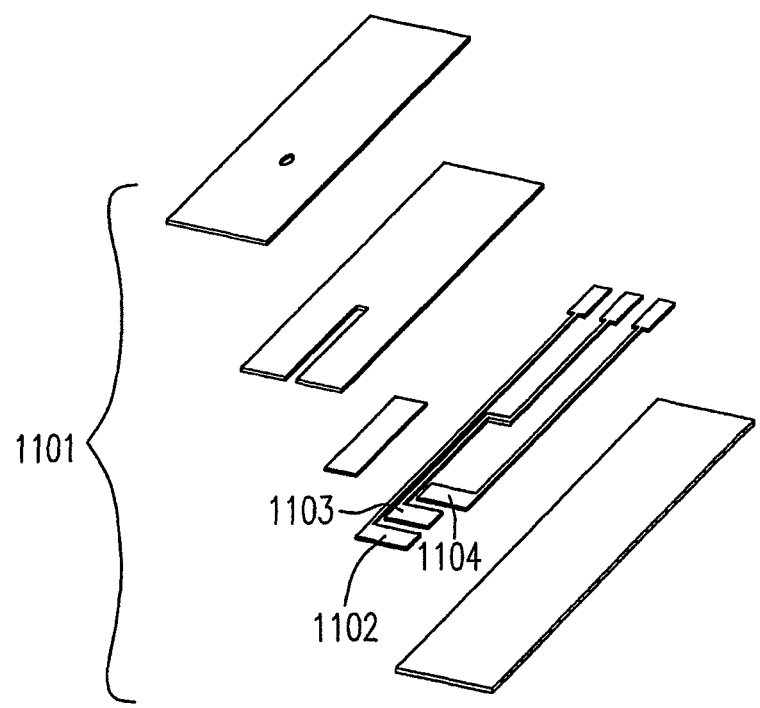
FIG. 11(B) is an explosion drawing of the electrochemical test strip shown in FIG. 11(A)
Figure 11C:
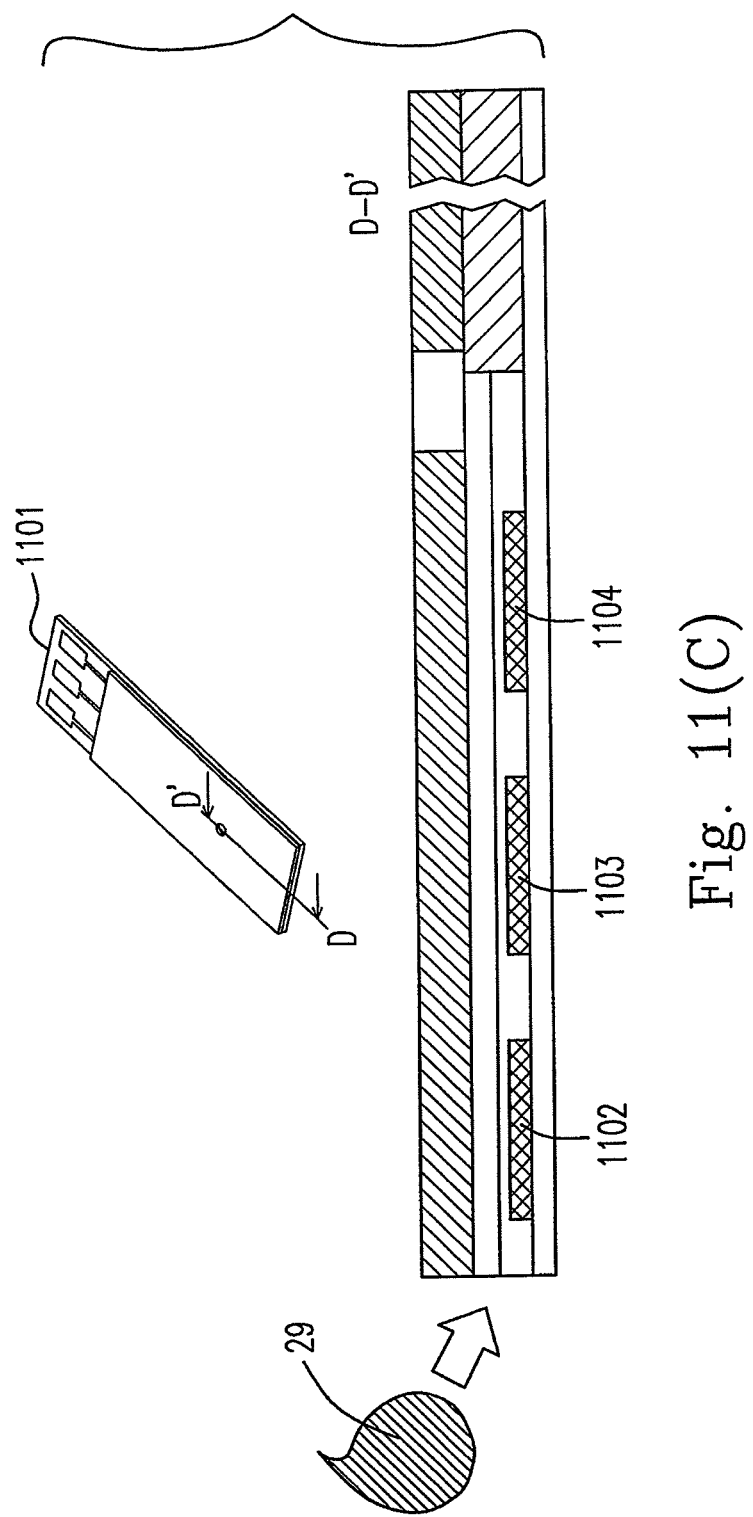
FIG. 11(C) is a sectional drawings of the electrochemical test strip shown in FIG. 11(A).

FIGS. 10(A) to 10(D) and FIGS. 11(A) to 11(C) respectively show electrochemical test strips 1001 and 1101, each of which has the thin-film electrodes. FIGS. 10(C) and (D) are sectional drawings of electrochemical test strip 1001 taken along the line C-C'. FIG. 11(C) is a sectional drawing of electrochemical test strip 1101 taken along the line D-D'. The formations and the structures of electrochemical test strips 1001 and 1101 are disclosed in U.S. Pat. No. 5,997, 817, U.S. Pat. No. 5,985,116 and EP 1098000, and thin film electrodes 1002, 1003, 1102, 1103 and 1104 can be formed by the screen printing or the metal deposition.

As shown in FIG. 10(C), when a blood sample 1008 starts to flow into channel 1010 of electrochemical test strip 1001 from sample entrance 1009, there will no sensing current be generated. However, with blood sample 1008 further flowing to cover electrode 1002 and contact electrode 1003 as shown in FIG. 10(D), the value of sensing current shown in FIGS. 6(A) to 6(I) can also be obtained accordingly so as to estimate whether the sample volume is sufficient for electrochemical test strip 1001.

A preferable embodiment is shown in FIGS. 11(A) to 11(C), where electrochemical test strip 1101 has a third thin-file electrode 1104 which is a thin-film reference electrode. Based on the present methods as above-mentioned, the value of sensing current shown in FIGS. 6(A) to 6(I) can also be obtained accordingly so as to estimate whether the sample volume is sufficient for electrochemical test strip 1101.

While the disclosure has been described in terms of what is presently considered to be the most practical and preferred embodiments, it is to be understood that the disclosure needs not be limited to the disclose embodiments. Therefore, it is intended to cover various modifications and similar arrangements included within the spirit and scope of the appended claims, which are to be accorded with the broadest interpretation so as to encompass all such modifications and similar structures.

What is claimed is:

1. A determining method for a distribution of a target sample in a sensor consisting of a first electrode and a second electrode, each of which is coated with a reagent layer, and a concentration of an analyte in the target sample, comprising the steps of:
   (a) providing the target sample flowing from the first electrode to the second electrode;
   (b) immediately providing a switching circuit having one of a first configuration with a first switch set and a second switch set, and a second configuration with the first switch set and the second switch set;
   (c) providing a digital signal to a control contact in the switching circuit to allow the switching circuit having the first configuration, such that the first switch set turns on when the second switch set turns off, for applying a first DC voltage with a voltage value across the first electrode and the second electrode for a first duration to make a potential of the first electrode higher than a potential of the second electrode, wherein the first electrode functions as a working electrode to generate a first Cottrell current, the second electrode functions as a counter electrode, and the target sample flows from the working electrode to the counter electrode;

(d) removing the first DC voltage for a first removing duration;

(e) reversing the digital signal to allow the switching circuit having the second configuration, such that the second switch sets turns on when the first switch set turns off, for applying a second DC voltage with a voltage value across the first electrode and the second electrode for a second duration to make the potential of the second electrode higher than the potential of the first electrode, wherein the second electrode functions as the working electrode to generate a second Cottrell current, the first electrode functions as the counter electrode, and the respective voltage values of the first and the second DC voltages are equal;

(f) removing the second DC voltage for a second removing duration;

(g) sequentially repeating steps (b) to (e) at least twice;

(h) adding up respective values of the first Cottrell currents and respective values of the second Cottrell currents respectively; and (i) obtaining a ratio of a sum of the respective values of the first Cottrell currents over a sum of the respective values of the second Cottrell currents to determine a distribution of the target sample on the first and the second electrodes and the concentration of the analyte in the target sample, whereby the distribution of the target sample is determined as long as a sufficient volume of the target sample is within a range between 0.45 µL and 0.8 µL.

2. A method according to claim 1, wherein the first and the second DC voltages are determined via cyclic voltammograms, and S/N ratios of the first DC voltage and the second DC voltage are not smaller than 1.

3. A method according to claim 1, wherein the reagent layer has an enzyme and an electron transfer mediator, and the enzyme makes the target sample generate a reaction being one selected from a group consisting of an oxidation, a reduction and a redox.

4. A method according to claim 1, wherein the first and second durations are between 3 ms to 20 ms.

5. A method according to claim 1, wherein the first and second durations are equal.

6. A method according to claim 1, wherein the first removing and the second removing durations are between 0 ms to 20 ms.

7. A method according to claim 1, wherein the first removing and the second removing durations are equal.

8. A method according to claim 1, wherein the first electrode and the second electrode have respective electrochemical reaction areas being equal to each other.

9. A method according to claim 8, wherein both the first and the second electrodes are fully covered thereon by the target sample when the ratio is 1.

10. A method according to claim 1, wherein the first and the second electrodes have respective electrochemical reaction areas, and the electrochemical reaction area of the first electrode is not equal to that of the second electrode.

11. A method according to claim 1, wherein the sensor is an electrochemical sensor.

12. A method according to claim 1, wherein the first Cottrell current is proportional to a surface area of the first electrode covered by the target sample, and the second Cottrell current is proportional to the surface area of the second electrode covered by the target sample.

13. A method according to claim 1, wherein the detection is effective when the ratio is between 0.3 and 3.0.

14. A method according to claim 1, wherein the value of the first Cottrell current and the value of the second Cottrell current are recorded during the first and the second durations respectively.

15. A determining method for a distribution of a target sample, comprising the steps of:

(a) providing a first and a second electrodes;

(b) providing the target sample flowing from the first electrode to the second electrode;

(c) providing a switching circuit having one of a first configuration with a first switch set and a second switch set, and a second configuration with the first switch set and the second switch set;

(d) providing a digital signal to a control contact in the switching circuit to allow the switching circuit having the first configuration, such that the first switch set turns on when the second switch set turns off, for applying a first DC voltage with a voltage value across the first electrode and the second electrode to make a potential of the first electrode higher than a potential of the second electrode and to generate a first sensing current, wherein the first electrode functions as a working electrode, the second electrode functions as a counter electrode, and the target sample flows from the working electrode to the counter electrode;

(e) removing the first DC voltage;

(f) reversing the digital signal to allow the switching circuit having the second configuration, such that the second switch set turns on when the first switch set turns off, for applying a second DC voltage having the voltage value across the first electrode and the second electrode to make the potential of the second electrode higher than the potential of the first electrode and to generate a second sensing current, wherein the second electrode functions as the working electrode, and the first electrode functions as the counter electrode; and (g) obtaining a ratio of a value of the first sensing current over a value of the second sensing current to determine the distribution of the target sample on the first and the second electrodes, whereby the distribution of the target sample is determined as long as a sufficient volume of the target sample is within a range between 0.45 µL, and 0.8 µL.

16. A method according to claim 15, wherein the first and the second electrodes are configured. on an electrochemical. strip.

17. A method according to claim 15, wherein the first and the second DC voltages are applied for a period for 3 ms to 20 ms.

18. A method according to claim 15, wherein the first and the second sensing currents are Cottrell currents.

19. A determining method, comprising the steps of:

(a) providing a first and a second electrodes;

(b) providing a target sample flowing from the first electrode to the second electrode;

(c) providing a switch circuit having one of a first configuration with a first switch set and a second switch set, and a second configuration with the first switch set and the second switch set;

(d) providing a digital signal to a control contact, in the switching circuit to allow the switching circuit having the first configuration, such that the first switch set turns on when the second switch set turns off, for applying a first DC voltage with a voltage value across the first electrode and the second electrode to make a potential of the first electrode higher than a potential of the second electrode, and to generate a first sensing current, wherein the first electrode functions as a working electrode, the second electrode functions as a counter electrode, and the target sample flows from the working electrode to the counter electrode;

(e) reversing the digital signal to allow the switching circuit having the second configuration, such that the second switch set turns on when the first switch set turns off, for applying a second DC voltage having the voltage value across the first electrode and the second electrode to make the potential of the second electrode higher than the potential of the first electrode, and to generate a second sensing current, wherein the second electrode functions as the working electrode, and the first electrode functions as the counter electrode; and (f) obtaining a ratio of a value of the first sensing current over a value of the second sensing current to determine the distribution of the target sample on the first and the second electrodes, whereby the distribution of the target sample is determined as long as a sufficient volume of the target sample is within a range between 0.45 µL and 0.8 µL.

* * * * *